US008979996B2

(12) United States Patent
Standke et al.

(10) Patent No.: US 8,979,996 B2
(45) Date of Patent: *Mar. 17, 2015

(54) COMPOSITION CONTAINING QUATERNARY AMINO-FUNCTIONAL ORGANOSILICON COMPUNDS AND PRODUCTION AND USE THEREOF

(71) Applicant: Evonik Degussa GmbH, Essen (DE)

(72) Inventors: Burkhard Standke, Loerrach (DE); Christian Wassmer, Hausen (DE); Tim Voegtlin, Schopfheim (DE); Irene Lippert, Rheinfelden (DE); Stefan Scharfe, Erlensee (DE); Heinz Lach, Rodenbach (DE); Christoph Batz-Sohn, Hanau-Mittelbuchen (DE); Steffen Hasenzahl, Hanau (DE)

(73) Assignee: Evonik Degussa GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/242,433

(22) Filed: Apr. 1, 2014

(65) Prior Publication Data

US 2014/0208981 A1   Jul. 31, 2014

Related U.S. Application Data

(63) Continuation of application No. 13/257,488, filed as application No. PCT/EP2010/053626 on Mar. 19, 2010, now Pat. No. 8,728,225.

(30) Foreign Application Priority Data

Apr. 20, 2009   (DE) .......................... 10 2009 002 477

(51) Int. Cl.
| | | |
|---|---|---|
| C09C 1/30 | (2006.01) | |
| C09D 7/12 | (2006.01) | |
| C07F 7/10 | (2006.01) | |
| C07F 7/18 | (2006.01) | |

(52) U.S. Cl.
CPC ............. C09C 1/3081 (2013.01); C07F 7/1892 (2013.01)
USPC ....................................... 106/287.11; 556/413

(58) Field of Classification Search
CPC .................................................... C09C 1/3081
See application file for complete search history.

(56) References Cited

U.S. PATENT DOCUMENTS

| 2,930,809 A | 3/1960 | Jex et al. |
| 3,560,385 A * | 2/1971 | Roth ............... 508/204 |
| 4,064,155 A * | 12/1977 | Speier ............. 556/413 |
| 4,282,366 A * | 8/1981 | Eudy ............... 556/413 |
| 4,390,712 A * | 6/1983 | Karl et al. ........ 556/413 |
| 4,394,378 A * | 7/1983 | Klein .............. 514/63 |
| 4,410,669 A * | 10/1983 | Panster et al. .... 525/474 |
| 4,526,996 A | 7/1985 | Kilgour et al. |
| 4,845,256 A * | 7/1989 | Mebes et al. ..... 556/413 |
| 4,933,327 A * | 6/1990 | Plueddemann et al. ........ 514/63 |
| 5,239,033 A * | 8/1993 | Panster et al. .... 528/9 |
| 5,352,791 A * | 10/1994 | Panster et al. .... 546/165 |
| 5,446,181 A * | 8/1995 | Uehara et al. .... 556/424 |
| 5,552,474 A * | 9/1996 | Panster et al. .... 524/588 |
| 5,698,726 A | 12/1997 | Rauleder et al. |
| 5,874,653 A * | 2/1999 | Van Kruchten ... 568/867 |
| 6,376,696 B1 | 4/2002 | Raab et al. |
| 6,641,870 B2 | 11/2003 | Bartkowiak et al. |
| 6,663,683 B2 | 12/2003 | Lortz et al. |
| 6,676,719 B2 | 1/2004 | Lortz et al. |
| 6,767,377 B2 | 7/2004 | Schumacher et al. |
| 6,773,697 B2 | 8/2004 | Hemme et al. |
| 6,773,814 B2 | 8/2004 | Schumacher et al. |
| 6,808,769 B2 | 10/2004 | Batz-Sohn et al. |
| 6,905,632 B2 | 6/2005 | Lortz et al. |
| 6,991,190 B2 | 1/2006 | Lortz et al. |
| 7,015,270 B2 | 3/2006 | Scharfe et al. |
| 7,083,769 B2 | 8/2006 | Moerters et al. |
| 7,244,302 B2 | 7/2007 | Schumacher et al. |
| 7,255,735 B2 | 8/2007 | Meyer et al. |
| 7,374,787 B2 | 5/2008 | Lortz et al. |
| 7,399,487 B2 | 7/2008 | Batz-Sohn et al. |
| 7,470,423 B2 | 12/2008 | Lortz et al. |
| 7,538,142 B2 | 5/2009 | Lortz et al. |
| 7,572,854 B2 | 8/2009 | Schneider et al. |
| 7,615,577 B2 | 11/2009 | Lortz et al. |
| 7,645,335 B2 | 1/2010 | Lortz et al. |
| 7,749,322 B2 | 7/2010 | Schumacher et al. |
| 7,780,777 B2 | 8/2010 | Perlet et al. |
| 7,781,520 B2 | 8/2010 | Standke et al. |
| 7,815,936 B2 | 10/2010 | Hasenzahl et al. |
| 7,834,073 B2 | 11/2010 | Standke et al. |
| 7,976,719 B2 | 7/2011 | Batz-Sohn et al. |
| 8,012,367 B2 | 9/2011 | Hasenzahl et al. |
| 8,039,110 B2 | 10/2011 | Jenkner et al. |
| 2002/0197311 A1 | 12/2002 | Hasenzahl et al. |
| 2003/0108580 A1 | 6/2003 | Hasenzahl et al. |
| 2003/0228271 A1 | 12/2003 | Batz-Sohn et al. |

(Continued)

FOREIGN PATENT DOCUMENTS

| DE | 199 28 127 | 5/2000 |
| DE | 10 2007 040 802 | 3/2009 |

(Continued)

OTHER PUBLICATIONS

International Search Report Issued Jun. 21, 2010 in PCT/EP10/053626 Filed Mar. 19, 2010.

*Primary Examiner* — Robert S Loewe
(74) *Attorney, Agent, or Firm* — Oblon, McClelland, Maier & Neustadt, L.L.P.

(57) ABSTRACT

The invention relates to a composition and to a method for the production thereof, comprising quaternary amino-functional organosilicon compounds, in particular in the form of oligomers and polymers, which can be present ranging from partially hydrolyzed form to completely hydrolyzed form, and which are in particular soluble in water, have a low VOC content, and to the use thereof.

20 Claims, No Drawings

(56) References Cited

U.S. PATENT DOCUMENTS

| | | |
|---|---|---|
| 2004/0240062 A1 | 12/2004 | Lortz et al. |
| 2005/0169861 A1 | 8/2005 | Lortz et al. |
| 2005/0265934 A1 | 12/2005 | Schumacher et al. |
| 2006/0104881 A1 | 5/2006 | Lortz et al. |
| 2006/0159635 A1 | 7/2006 | Meyer et al. |
| 2006/0159636 A1 | 7/2006 | Meyer et al. |
| 2006/0159637 A1 | 7/2006 | Meyer et al. |
| 2006/0163533 A1 | 7/2006 | Batz-Sohn et al. |
| 2006/0194976 A1 | 8/2006 | Kornek |
| 2006/0223962 A1* | 10/2006 | Getman et al. ............ 528/10 |
| 2006/0229210 A1 | 10/2006 | Neugebauer et al. |
| 2006/0292192 A1 | 12/2006 | Hasenzahl et al. |
| 2007/0110906 A1 | 5/2007 | Edelmann et al. |
| 2007/0231280 A1 | 10/2007 | Schumacher et al. |
| 2007/0297998 A1 | 12/2007 | Meyer et al. |
| 2008/0009643 A1 | 1/2008 | Mehta et al. |
| 2008/0058489 A1 | 3/2008 | Edelmann et al. |
| 2008/0095724 A1 | 4/2008 | Hasenzahl et al. |
| 2008/0187673 A1 | 8/2008 | Standke et al. |
| 2008/0206572 A1 | 8/2008 | Edelmann et al. |
| 2008/0213325 A1 | 9/2008 | Schumacher et al. |
| 2008/0221318 A1 | 9/2008 | Edelmann et al. |
| 2008/0249237 A1 | 10/2008 | Hager et al. |
| 2008/0264299 A1 | 10/2008 | Lortz et al. |
| 2009/0005518 A1 | 1/2009 | Just et al. |
| 2009/0007818 A1 | 1/2009 | Militz et al. |
| 2009/0022898 A1 | 1/2009 | Standke et al. |
| 2009/0030162 A1 | 1/2009 | Mueh et al. |
| 2009/0047225 A1 | 2/2009 | Hasenzahl et al. |
| 2009/0069464 A1 | 3/2009 | Standke |
| 2009/0131694 A1 | 5/2009 | Schumacher et al. |
| 2009/0186053 A1 | 7/2009 | Meyer et al. |
| 2009/0261309 A1 | 10/2009 | Lortz et al. |
| 2010/0117021 A1 | 5/2010 | Batz-Sohn et al. |
| 2010/0119851 A1 | 5/2010 | Giessler-Blank et al. |
| 2010/0159144 A1 | 6/2010 | Standke et al. |
| 2010/0191001 A1 | 7/2010 | Wassmer et al. |
| 2010/0209339 A1 | 8/2010 | Schumacher et al. |
| 2010/0209719 A1 | 8/2010 | Borup et al. |
| 2010/0233392 A1 | 9/2010 | Batz-Sohn et al. |
| 2010/0308287 A1 | 12/2010 | Lortz et al. |
| 2011/0143147 A1 | 6/2011 | Edelmann et al. |
| 2011/0144226 A1 | 6/2011 | Spyrou et al. |
| 2011/0259240 A1 | 10/2011 | Jenkner et al. |
| 2011/0268899 A1 | 11/2011 | Albert et al. |

FOREIGN PATENT DOCUMENTS

| | | |
|---|---|---|
| EP | 0 741 137 | 11/1996 |
| WO | 2005 047298 | 5/2005 |
| WO | 2008 004243 | 1/2008 |

* cited by examiner

COMPOSITION CONTAINING QUATERNARY AMINO-FUNCTIONAL ORGANOSILICON COMPUNDS AND PRODUCTION AND USE THEREOF

This application is a Continuation of U.S. application Ser. No. 13/257,488, filed on Oct. 21, 2011, now allowed, which is a National Stage of International Application No. PCT/EP2010/053626, filed on Mar. 19, 2010.

The invention relates to a novel aqueous composition and processes for its production comprising quaternary amino-functional organosilicon compounds, particularly in the form of oligomers and polymers, which can be present in partially hydrolyzed to completely hydrolyzed form, and particularly are water-soluble, and the compositions have only an extremely low VOC content, and also the use thereof, particularly—but not exclusively—in papercoating slips, for cationization of inkjet coatings, for finishing fiber materials and/or textiles, for improving the dyeability of substrates, for example in the case of textile fibers, yarns, paper, foils or else correspondingly coated substrates, for inhibiting/suppressing the growth of microorganisms or an electrostatic charge buildup to mention but a few particularly advantageous possibilities for use.

In general, organofunctional alkoxysilanes with quaternary nitrogen functionality, i.e., with a cationic group containing an organofunctionalized nitrogen, are well known. The quaternary nitrogen has a cationic functionality irrespective of the pH. Hitherto, preparation thereof was only possible via costly and inconvenient processes, for example under elevated pressure in an autoclave. A further disadvantage of these alkoxysilanes is the release of hydrolysis alcohols into the environment in the course of their use of known water-based application solutions.

The preparation of cationic organosilanes and their partial use in aqueous phases is reported in the following documents. DE 881654 discloses the preparation of quaternary silanes in an autoclave under anhydrous conditions. Further processes are disclosed by NL 6517163 for preparing quaternary methylarylsilanes, DE 1262272 discloses the preparation of corresponding silicones. Similarly, DE 2221349, DE 2648240, U.S. Pat. No. 4,035,411, U.S. Pat. No. 4,005,118 and U.S. Pat. No. 4,005,119 disclose processes for preparing quaternary silanes.

The use of quaternary amino-functional alkoxysilanes for inhibiting the growth of microorganisms is described by DE 2222997, DE 2229580 and DE 2408192. An improved dyeability of difficult-to-dye materials, such as Teflon or else leather, through using corresponding silanes is disclosed by GB 882067. The preparation of quaternary functionalized organosilanes is in each case effected in aprotic organic solvents or under moisture exclusion and under elevated pressure. The silanes prepared by these processes, or aqueous formulations thereof, contain large amounts of solvent. This leads in many applications to appreciable disadvantages, such as a low flashpoint, which requires explosion protection, or creates a cause of environmental damage through a high VOC burden.

EP 0054748 discloses a process wherein for example 3-chloropropyltriethoxysilane is reacted with aqueous trimethylamine as tertiary amine in an autoclave under elevated pressure. The reaction needs to be carried out under elevated pressure in an autoclave because of the necessary high reaction temperature of 120° C. or higher. The water-based formulations contain appreciable amounts of VOC through use of alkoxy-functional silanes and alcohol-water mixtures as solvents. Examples 1, 2, 3, 6, 7, 8, 9 and 10 suggest that VOC contents in the final formulations are between about 16% and 40% by weight. Examples 4, 5 and 11 proceed from, respectively bromoalkyl- and iodoalkyl-functional organosilanes and can be regarded as industrially irrelevant because of the environmental issues associated with the remaining counteranions iodide and bromide.

WO 2008/076839 utilizes a commercially available quaternary silane (AEM 5772, Aegis Antimicrobial agent, active ingredient: 3-(trimethoxysilyl)propyldimethyl-octadecylammonium chloride), which contains 12% of methanol. U.S. Pat. No. 4,845,256 discloses a process for preparing quaternary silanes alkaline earth metal iodide catalysts for the reaction of chloroalkyl-functional alkoxysilanes and tertiary amines. The process described proceeds under normal pressure at a temperature of 100° C., but is disadvantageous in two respects. First, the environmentally problematical alkaline earth metal iodides are used in appreciable amounts; secondly, the aqueous application solutions contain appreciable amounts of VOC, such as hydrolysis methanol and glycols which are used in the process therein and remain in the application solution. The product described in example 1 generates more than 50% of VOC in an aqueous application solution (based on the starting solution of the quaternary methoxysilane [3-(trimethoxysilyl)propyldecyldimethylammonium chloride] dissolved in propylene glycol monomethyl ether).

The following documents disclose the use of cationic amino-functional silanes for cationization of inkjet paper applications.

WO 2005/009745 A2 discloses cationic aluminum oxide particles with amino-functional silanes. US 20030175451 relates to the coating of silica with silanes to improve performance in inkjet applications. US 20050170109 discloses the treatment of silica with aminoalkoxysilanes and use thereof for inkjet papers and DE 10 2007 012578 A1 discloses the preparation of cationic silica dispersions using primary, secondary or tertiary aminosilanes and use thereof for coatings. WO 2005/009745 A2, US 2005/170109 A1 and US 2003/175451 mention in general the possibility of using a quaternary amino-functional alkoxysilane, such as trimethoxysilanepropyl-N,N,N-trimethylammonium chloride, or an N,N,N-tributylammonium chloride-substituted silane. Concrete examples are not disclosed.

DE 102007040802 A1 describes the successful use of low-VOC, protonated amino-functional silanol group-containing siloxane systems (hydrosils) in the cationization of papercoating slips. The protonation of the amino function of these systems is substantially pH-dependent. Therefore, the performance of these applications is still in need of improvement. The processability of papercoating slips is governed by their viscosity and solids content. The higher the viscosity, the greater the inconvenience and cost of processing, although at the same time a high solids content is desired for the systems for capacity reasons.

There accordingly continues to be a need for VOC-reduced quaternary amino-functional organosilicon compounds which make it possible to set a low viscosity coupled with a simultaneously high solids content of dispersions, for example silica dispersions, more particularly papercoating slips.

The problem addressed by the present invention was that of providing VOC-reduced quaternary aminoalkyl-functional organosilicon compounds, or compositions containing these, and also an economical process for production thereof which preferably permits an economical setting of the desired viscosity and of the solids content in the process.

The problem is solved according to the present invention in accordance with the recitations in the claims. More particularly, the problem is solved by the inventive composition corresponding to the features of claims 16 and 21 and also by the inventive production process according to claim 1. Preferred embodiments are recited in the dependent claims and also in the description.

The problem was solved, surprisingly, by reacting haloalkyl-functional alkoxysilanes, optionally together with further organofunctional silicon compounds, such as organofunctional alkoxysilanes and/or condensation-capable oligomeric or polymeric organofunctional silicon compounds, together with tertiary amines in the presence/under addition of a defined amount of water and removing the resulting hydrolysis alcohol at least partially and preferably removing the hydrolysis alcohol essentially completely. The occurring quaternization reaction and at least partial hydrolysis and any partial condensation, i.e., including co- or block condensation, is advantageously carried out under temperature control, i.e., heating or cooling is applied as necessary, and the reaction mixture is suitably stirred. In the process, an originally tertiary organofunctionally substituted nitrogen atom of the tertiary amine becomes a quaternary nitrogen atom, more particularly by formation of oligomeric or polymeric quaternary amino-functional organosilicon compounds which are obtainable according to the present invention and which are more particularly elucidated hereinbelow.

Furthermore, hydrolysis alcohol formed during or after the hydrolysis reaction can be distillatively removed from the aqueous reaction mixture and fresh water added as necessary, in which case the present invention provides an aqueous solution of said quaternary amino-functional organosilicon compounds, preferably quaternary alkylammonium-functional organosilicon compounds (hereinafter also referred to as composition or silane system for short) which is ready to use or suitable for advantageous application.

Subject compositions advantageously have a VOC content of distinctly below 12% by weight to 0% by weight, based on the overall composition. The content of volatile organic compounds (VOCs), more particularly solvents, such as hydrolysis alcohol, in a composition according to the present invention is preferably below 5% by weight, more preferably below 2% by weight, even more preferably below 1% by weight and more particularly in the range from 0.001 to 0.5% by weight, based on the overall composition. Therefore, subject compositions are hereinafter also referred to as VOC-free for short. Furthermore, the compositions obtainable according to the present invention, which contain quaternary aminoalkyl-functional organosilicon compounds, are thinnable with water in virtually any ratio, more particularly between 1:100 to 100:1 and also all ratios therebetween.

The quaternary amino-functional organosilicon compounds can be more particularly oligomeric/polymeric organosilicon compounds which, per molecule, include at least one quaternary aminoalkyl-functional radical, more particularly at least one quaternary alkylammonium-functional radical, in which case at least one of the aminoalkyl radicals comprises a silicon atom, more particularly a silanol group or an organosilanol, an oligomer or polymer of organosilicon compounds.

The invention is an advantageous way of providing novel VOC-reduced (volatile organic compound) organofunctional silane systems, hereinbelow called compositions, with quaternary nitrogen functionality ($NR_4^+$, where the R groups can be the same or different and at least one R group is silylated and R is covalently bonded to N via a C-atom), which are advantageously providable at normal pressure and in high yield. At least one R radical comprises organosilicon groups, optionally R may also contain further heteroatoms. Altogether, the silane system according to the present invention may evince linear, branched, cyclic and/or spatially crosslinked structures or structural regions with M-, D-, T-structures or else, depending on the method of making, Q-structures. When tetraalkoxysilane is added to the reaction mixture, for example.

Condensation products for the purposes of the invention comprehend not only homo- but also co-condensation products from the reaction of hydrolyzed alkoxysilanes, silanols, oligomeric or else polymeric SiOH-functional silicon compounds or organosilicon compounds, and also condensation products involving the participation of block co-condensates.

It is further surprising that the reactions mentioned as taking place in the course of the process of the present invention, such as quaternization, hydrolysis and, where applicable, condensation, can be carried out virtually simultaneously in one reaction mixture at relatively low reaction temperatures below 100° C. and hence particularly advantageously. A further particular advantage of the process according to the present invention is that the conversion can take place at these relatively low temperatures at normal pressure. Therefore, the use of costly and inconvenient autoclaves is unnecessary in the process of the present invention, since, depending on the tertiary amines used and their boiling point, the reaction is advantageously carried out at normal pressure when the boiling point of the amines is above the reaction temperature. The boiling point of the tertiary amines used, particularly of formula II, as elucidated hereinbelow, is preferably above 85° C., more preferably above 100° C. and more particularly above 120° C.

It is particularly surprising that not only the quaternization reaction at the haloalkyl group of the starting haloalkyl-functional silane of formula I but also the hydrolysis and also condensation/co-condensation of the organosilicon compounds in the reaction mixture take place not just simultaneously, i.e., as a one-pot reaction, but moreover also substantially selectively.

Surprisingly, the problem was solved by a process for preparing an inventive composition containing quaternary aminoalkyl-functional organosilicon compounds by reacting, at least one haloalkyl-functional silane of formula I and/or
optionally its hydrolysis and/or condensation products,
i.e., including possible homo-, co-, block or block co-condensates, $(R^1O)_{3-x-y}(R^2)_xSi[(R^3)_nCH_2Hal]_{1+y}$     (I),

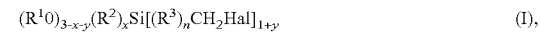

where the $R^1$ groups are the same or different and $R^1$ represents a hydrogen, a linear, branched, or cyclic alkyl group having 1 to 8 carbon atoms, an aryl, arylalkyl or acyl group, the $R^2$ groups are the same or different and $R^2$ represents a linear, branched or cyclic alkyl group having 1 to 8 carbon atoms, an aryl, arylalkyl or acyl group, the $R^3$ groups are the same or different and $R^2$ signifies a linear, branched or cyclic alkylene group having 1 to 18 carbon atoms, i.e., a bivalent alkyl group having 1 to 18 carbon atoms, wherein the alkylene group may be substituted or contain olefinic C—C linkages, preferably —$CH_2$—, —$(CH_2)_2$—, —$CH_2CH(CH_3)$—, n is equal to 0 or 1 and Hal represents chlorine or bromine, and x is equal to 0, 1 or 2, y is equal to 0, 1 or 2 and (x+y) is equal to 0, 1 or 2, with a tertiary amine of the general formula II in the presence and/or under addition of a defined amount of water, $N(R^4)_3$     (II),

where the $R^4$ groups are the same or different and $R^4$ represents a group $(R^1O)_{3-x-y}(R^2)_xSi[(R^3)_nCH_2—]_{1+y}$, where $R^1$, $R^2$, $R^3$, n, x, y and (x+y) likewise have the aforementioned meaning, or represents a linear, branched or cyclic alkyl group having 1 to 30 carbon atoms which may additionally be substituted, preferably with at least one group from the series $-N(R^5)_2$, where the $R^5$ groups are the same or different and $R^5$ represents a hydrogen, a linear, branched or cyclic alkyl group having 1 to 8 carbon, atoms, an aminoalkyl group or $(R^1O)_{3-x-y}(R^2)_xSi[(R^3)_nCH_2-]_{1+y}$, $-SR^6$, where the $R^6$ groups are the same or different and $R^6$ represents a hydrogen, a linear, branched or cyclic alkyl group having 1 to 8 carbon atoms or $(R^1O)_{3-x-y}(R^2)_xSi[(R^3)_nCH_2-]_{1+y}$, or optionally its hydrolysis and/or condensation products, $-OR^1$ or $(R^1O)_{3-x}(R^2)_xSi[(R^3)_nCH_2-]$ or optionally its hydrolysis and/or condensation products, where the groups $R^1$, $R^2$, $R^3$, x and n independently have the meaning already mentioned above, where optionally two $R^4$ groups are in turn linked together and combine with the nitrogen of the tertiary amine to form a cycle, and the resultant hydrolysis alcohol is at least partially removed.

In addition, however, the subject process can also utilize further components, for example as a catalyst, as a diluent or as an input component—to mention but a few of the possibilities.

The present invention accordingly provides a process for preparing a composition containing quaternary amino-functional organosilicon compounds, characterized in that it comprises reacting as component A (i) at least one haloalkyl-functional alkoxysilane of the general formula I

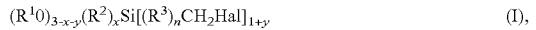

$(R^1O)_{3-x-y}(R^2)_xSi[(R^3)_nCH_2Hal]_{1+y}$ (I), where the $R^1$ groups are the same or different and $R^1$ represents a hydrogen, a linear, branched, or cyclic alkyl group having 1 to 8 carbon atoms, an aryl, arylalkyl or acyl group, the $R^2$ groups are the same or different and $R^2$ represents a linear, branched or cyclic alkyl group having 1 to 8 carbon atoms, an aryl, arylalkyl or acyl group, the $R^3$ groups are the same or different and $R^2$ signifies a linear, branched or cyclic alkylene group having 1 to 18 carbon atoms, n is equal to 0 or 1 and Hal represents chlorine or bromine, and x is equal to 0, 1 or 2, y is equal to 0, 1 or 2 and (x+y) is equal to 0, 1 or 2, or (ii) a hydrolysis or condensation product of at least one alkoxysilane of the aforementioned general formula I or (iii) a mixture of at least one alkoxysilane of the aforementioned general formula I and a hydrolysis and/or condensation product of at least one alkoxysilane of the aforementioned general formula I with a tertiary amine of the general formula II as component B,

$N(R^4)_3$ (II), where the $R^4$ groups are the same or different and $R^4$ represents a group $(R^1O)_{3-x-y}(R^2)_xSi[(R^3)_nCH_2-]_{1+y}$, where $R^1$, $R^2$, $R^3$, n, x, y and (x+y) likewise have the aforementioned meaning, or represents a linear, branched or cyclic alkyl group having 1 to 30 carbon atoms which may additionally be substituted, where optionally two $R^4$ groups are in turn linked together and combine with the nitrogen of the tertiary amine to form a cycle, in the presence of a defined amount of water, and removing the resulting hydrolysis alcohol at least partially from the system.

According to the present invention, it is advantageously a silane of formula I, more particularly a chloroalkyl-functional silane optionally its hydrolysis and/or condensation product, which is mixed in the process with a tertiary amine of formula II, there ensues in the presence of 0.5 to 500 mol of water per mol of silicon atoms a quaternization—on the nitrogen atom—and at least partially hydrolysis and possibly condensation (of the alkoxysilanes to silanol groups, followed by a condensation to form Si—O—Si bridges)—of the compounds of formula I and II. The reaction can preferably be carried out in a kind of "one-pot reaction", for example batchwise, hydrolysis alcohol can be distilled off during the reaction and further water added at essentially the same time. The pressure in the reaction vessel can also be reduced with increasing reaction duration, i.e., the volatile organic fractions, more particularly the hydrolysis alcohol which is formed, can be removed, at least proportionally, from the system by distillation under reduced pressure.

Furthermore, the reaction mixture of components A and B may have added to it as a further input component C, at least one further hydrolyzable silicon compound, preferably an organoalkoxy-functional silicon compound, its hydrolysis, homo-, co-, block co-condensate or mixtures thereof.

The inventive quaternization reaction, hydrolysis and at least partially ensuing condensation, i.e., including possible, homo-, co-, block or block co-condensation, will make oligomeric and/or polymeric organosilicon compounds having at least one quaternary alkylammonium-functional radical or else cyclic compounds with quaternary nitrogen, for example an N-alkylpyrimidinium compound, obtainable according to chemical understanding.

According to the present invention, the process is carried out in the presence and more particularly under addition of a defined amount of water in that more particularly 5 to 25 mol of water per mol of silicon atoms are added, preferably 10 to 20 mol of water per mol of silicon atoms and more preferably 12 to 17 mol of water per mol of silicon atoms. In general, the water can be added continuously or discontinuously, in which case it will prove particularly advantageous to add the water discontinuously, preferably portionwise, specifically in 1 to 10 portions, preferably 2 to 5 portions and more preferably in 3 portions. The process of the present invention thus preferably utilizes water in an amount of 0.5 to 500 mol of water per mol of silicon atoms present in the reaction mixture, preferably 5 to 25 mol of water per mole of hydrolyzable silicon atoms concerning the used components A and also optionally B and/or C, particularly preferably 10 to 20 mol of water per mol of said silicon atoms, more particularly 12 to 17 mol of water per mol of said silicon atoms. It is further preferable in the process of the present invention when the water is metered continuously or discontinuously into the reaction mixture of the input components A, B and optionally C, in particular the water is added discontinuously under stirring, more preferably portionwise, in 1 to 10 portions, more particularly in 2 to 5 portions. It is further preferable, in the process, for the water to be added as rapidly as possible to the silane of formula I, the tertiary amine of formula II or the mixture comprising the silane and the amine. Surprisingly, the time and/or the portionwise addition of the water can also have a particularly good influence on the viscosity of the composition with an otherwise unchanged content of quaternary amino-functional organosilicon compounds. Preferably, the addition of water takes place very directly subsequent to mixing the compounds of formula I and II. Adding the entire amount of water in one step to the reaction can lead to the formation of insoluble precipitates which have to be expensively and inconveniently filtered off to produce solutions of the composition for example.

More particularly, the reaction according to the invention is carried out at a pressure of 1 mbar to 1.1 bar, preferably at ambient pressure (normal pressure), and a temperature of 20 and 150° C., preferably in the range from 40 to 120° C., more preferably in the range from 60 to 100° C. and more particularly in the range from 80 to 95° C. It is particularly preferable to perform the reaction at a reaction temperature below 100° C. and at normal pressure, more particularly around 1013.25 hPa plus/minus 25 hPa.

The present reaction can also be carried out in the presence of a catalyst, more particularly under addition of a hydrolysis and/or condensation catalyst, for example—but not exclusively—an organic or inorganic acid, such as formic acid, acetic acid, propionic acid, citric acid, hydrogen chloride, as gas, concentrated or aqueous hydrochloric acid, boric acid, nitric acid, sulfuric acid, phosphoric acid to name but a few.

In addition, to carry out the reaction, the reaction mixture of components A and B or a reaction mixture of components A, B and at least one further component C can have added to it a diluent, for example an alcohol, such as methanol, ethanol, isopropanol, in which case the diluent added is suitably removed again from the system as it were in the course of the removal of the hydrolysis alcohol formed in the course of the reaction.

The hydrolysis alcohol formed in the course of the reaction is removed essentially completely, preferably by distillation, more particularly during the reaction. In a particularly preferred process mode, the distillatively removed amount of hydrolysis alcohol and water can be compensated in the azeotropic mixture by further addition of water, say.

Advantageously, in the process of the present invention, volatile solvent/diluent medium and any groups hydrolyzable to volatile solvent, more particularly hydrolysis alcohol, are removed down to a level in the overall composition of below 12% by weight to 0% by weight, preferably below 10% by weight, more preferably below 5% by weight and even more preferably in the range from 2% by weight to 0.0001% by weight and more particularly in the range from 1% to ≤0.5% by weight, wherein the removing of volatile solvent/diluent medium can be effected during the reaction and/or thereafter by distillation, more particularly under reduced pressure in the range from 1 to 1000 mbar and preferably from 80 to 300 mbar. Suitably, however, the pressure can also be lowered in the course of the reaction from ambient pressure to a reduced pressure.

The purely quaternization reaction of compounds of formula I, or as per component A and of the tertiary amine of formula II as per component B to form at least one said quaternary aminoalkyl-functional silane is shown in idealized form in what follows, wherein the formulae I and II are as defined above:

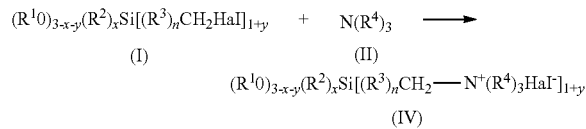

Furthermore, during the reaction, hydrolysis and also condensation of compounds of formulae I, II and/or resultant quaternization products (IV) can lead to the formation of so-called oligomeric and/or polymeric quaternary aminofunctional organosilicon compounds as elucidated hereinbelow.

It is believed, in common with chemical understanding, that, under the reaction conditions according to the present invention, the reaction of compounds of formulae I and II proceeds by quaternization and at least partial hydrolysis, as idealized hereinbelow (the R groups may be alkyl or aminoalkyl, for example—but nonexclusively—methyl, ethyl, propyl, butyl, N,N-dimethylaminoethyl):

Quaternization and partial/complete hydrolysis:

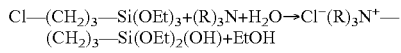

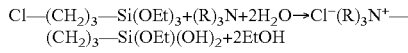

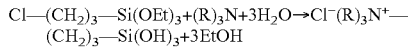

Condensation:

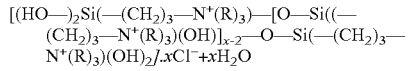

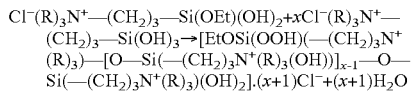

x can be a number from 2 to ∞.

It is particularly preferable for the inventive reaction of silanes of formula I within the meaning of component A with tertiary amines of formula II as component B, optionally in the presence of at least one silicon compound of formula III as component C of the reaction mixture, in the process of the present invention to take place exclusively in the presence of moisture or water, in which case hydrolysis, homo- and/or co-condensation products of II and optionally III are also encompassed and from 0.5 mol to 500 mol and more preferably from 0.5 to 200 mol of water are preferably used per mol of silicon.

Component A in the process of the present invention may advantageously comprise for example—but not exclusively—a silicon compound from the series 3-chloropropyltrimethoxysilane, 3-chloropropyltriethoxysilane, 3-chloropropylmethyldimethoxysilane, 3-chloropropylmethyldiethoxysilane, 3-chloropropyldimethylethoxysilane or 3-chloropropyldimethylmethoxysilane or a hydrolysis or condensation product of the aforementioned alkoxysilanes.

In general, any compounds which are known to a person skilled in the art as containing tertiary amino groups are useful as component B for producing the composition of the present invention, preferably when their boiling point is above 85° C. and more preferably when their boiling point is above 100° C. or above 120° C.

One particular advantage of the process according to the present invention is the low reaction temperature, which is between 20 to 150° C., more particularly between 40 to 120° C., preferably between 60 to 100° C. and more preferably between 80 to 95° C., and the reaction is preferably carried out essentially at normal pressure. According to the present invention, the reaction can be carried out at a temperature below 100° C. and preferably at normal pressure.

Component B in the process of the present invention may advantageously comprise for example—but not exclusively—at least one tertiary amine selected from the series tetramethylethylenediamine, pentamethyldiethylenetriamine, hexadecyldimethylamine, octadecyldimethylamine, tetradecyldimethylamine, dodecyldimethylamine, decyldimethylamine, octyldimethylamine, tetraethylethylenediamine, pentaethyldiethylenetriamine, hexadecyldiethylamine, octadecyldiethylamine, tetradecyldiethylamine, dodecyldiethylamine, decyldiethylamine, octyldiethylamine, isohexadecyldimethylamine, isooctadecyldimethylamine, isotetradecyldimethylamine, isododecyldimethylamine, isodecyldimethylamine, isooctyldimethylamine, isotetraethylethylenediamine, isopentaethyldiethylenetriamine, isohexadecyldiethylamine, isooctadecyldiethylamine, isotetradecyldiethylamine, isododecyldiethylamine, isodecyldiethylamine, isooctyldiethylamine, tris(trimethoxysilylpropyl)amine, tris(triethoxysilylpropyl)amine, tris(trimethoxysilylmethyl)amine, tris(triethoxysilylmethyl)amine.

The reaction of the haloalkyl-functional silane, more particularly the chloroalkylsilane of formula I, is preferably carried out using a molar ratio of haloalkyl group to tertiary amine group, more particularly of an amine of formulae II, V and/or VI, in the range from 2:1 to 1:m, where m is the number of tertiary amine groups, and more particularly m is an integer between 1 to 100. It is accordingly preferable for the process of the present invention when components A and B are used in a ratio, wherein the molar ratio of the silicon compound within the meaning of formula I to the tertiary amine compound within the meaning of formula II is in the range from 2:1 to 1:m, wherein m is the number of tertiary amine groups of formula II and m is an integer between 1 to 100, preferably in the range from 1 to 10, more preferably 1, 2, 3, 4, 5, 6 or 7 and more particularly 1 or 2.

In addition, the process of the present invention can be advantageously utilized in components A and C, which will be further particularized hereinbelow, in a molar ratio of 1:<4, preferably 1:0 to 2, more preferably 1:0.001 to 1 and more particularly 1:0.1 to 0.5.

Component C in the process of the present invention can comprise for example—but not exclusively—at least one silicon compound from the series silicon tetrachloride, tetramethoxysilane, tetraethoxysilane, tetrapropoxysilane, methyltrimethoxysilane, methyltriethoxysilane, ethyltrimethoxysilane, ethyltriethoxysilane, n-propyltrimethoxysilane, n-propyltriethoxysilane, n-butyltrimethoxysilane, i-butyltrimethoxysilane, n-butyltriethoxysilane, i-butyltriethoxysilane, n-octyltrimethoxysilane i-octyltrimethoxysilane, n-octyltriethoxysilane, i-octyltriethoxysilane, hexadecyltrimethoxysilane, hexadecyltriethoxysilane, vinyltriethoxysilane, vinyltrimethoxysilane, vinyltris(2-methoxyethoxy)silane, phenyltrimethoxysilane, phenyltriethoxysilane, tridecafluoro-1,1,2,2-tetrahydrooctyltrimethoxysilane, tridecafluoro-1,1,2,2-tetrahydrooctyltriethoxysilane, 3-mercaptopropyltrimethoxysilane, 3-mercaptopropyltriethoxysilane, 1-mercaptomethyltrimethoxysilane, 1-mercaptomethyltriethoxysilane, 3-glycidyloxypropyltriethoxysilane, 3-glycidyloxypropyltrimethoxysilane, 3-methacryloxyisobutyltrimethoxysilane, 3-methacryloxyisobutyltriethoxysilane, 3-methacryloxypropyltrimethoxysilane, 3-methacryloxypropyltriethoxysilane, 3-methacryloxypropylmethyldimethoxysilane, 3-methacryloxypropylmethyldiethoxysilane, 3-ureidopropyltriethoxysilane, 3-ureidopropyltrimethoxysilane, 3-aminopropyltrimethoxysilane, 3-aminopropyltriethoxysilane, 3-aminopropylmethyldimethoxysilane, 3-aminopropylmethyldiethoxysilane, 1-aminomethyltrimethoxysilane, 1-aminomethyltriethoxysilane, 2-aminoethyltrimethoxysilane, 2-aminoethyltriethoxysilane, 3-aminoisobutyltrimethoxysilane, 3-aminoisobutyltriethoxysilane, N-n-butyl-3-aminopropyltriethoxysilane, N-n-butyl-3-aminopropylmethyldiethoxysilane, N-n-butyl-3-aminopropyltrimethoxysilane, N-n-butyl-3-aminopropylmethyldimethoxysilane, N-n-butyl-1-aminomethyltriethoxysilane, N-n-butyl-1-aminomethylmethyldimethoxysilane, N-n-butyl-1-aminomethyltrimethoxysilane, N-n-butyl-1-aminomethylmethyltriethoxysilane, benzyl-3-aminopropyltrimethoxysilane, benzyl-3-aminopropyltriethoxysilane, benzyl-2-aminoethyl-3-aminopropyltrimethoxysilane, benzyl-2-aminoethyl-3-aminopropyltriethoxysilane, N-formyl-3-aminopropyltriethoxysilane, N-formyl-3-aminopropyltrimethoxysilane, N-formyl-1-aminomethylmethyldimethoxysilane, N-formyl-1-aminomethylmethyldiethoxysilane, diaminoethylene-3-propyltrimethoxysilane, diaminoethylene-3-propyltriethoxysilane, triaminodiethylene-3-propyltrimethoxysilane, triaminodiethylene-3-propyltriethoxysilane, (2-aminoethyl-amino)ethyltrimethoxysilane, (2-aminoethylamino)ethyltriethoxysilane, (1-aminoethyl-amino)methyltrimethoxysilane, (1-aminoethylamino)methyltriethoxysilane, tris(trimethoxysilylpropyl)amine, tris(triethoxysilylpropyl)amine, tris(trimethoxysilyl-methyl)amine, tris(triethoxysilylmethyl)amine, bis(trimethoxysilylpropyl)amine, bis(triethoxysilylpropyl)amine, bis(diethoxymethylsilylpropyl)amine, bis(dimethoxy-methylsilylpropyl)amine, bis(triethoxysilylmethyl)amine, bis(trimethoxysilyl-methyl)amine, bis(diethoxymethylsilylmethyl)amine, bis(dimethoxymethylsilyl-methyl)amine, $(H_3CO)_3Si(CH_2)_3NH(CH_2)_2NH(CH_2)_3Si(OCH_3)_3$, $(H_3CO)_3Si(CH_2)_3NH(CH_2)_2NH(CH_2)_2NH(CH_2)_3Si(OCH_3)_3$, $(H_3CO)_2(CH_3)Si(CH_2)_3NH(CH_2)_2NH(CH_2)_3Si(OCH_3)_2(CH_3)$, $(H_3CO)_3 (CH_3)Si(CH_2)_3NH(CH_2)_2NH(CH_2)_2NH(CH_2)_3Si(OCH_3)_2 (CH_3)$, or a mixture of at least two of the aforementioned compounds or a hydrolysis/condensation product of one of the aforementioned compounds or a hydrolysis, condensation, co-, block or block co-condensation product of at least two of the aforementioned compounds.

The hydrolysis alcohol formed by hydrolysis in the course of the reaction in the process of the present invention and optionally added solvent/diluent medium, is suitably removed by distillation, and it is preferable to add further water in order, more particularly, that the previously distillatively removed amount of water, hydrolysis alcohol and solvent may be essentially replaced. Alternatively, any desired amount of water can be added. The distillation is preferably carried out under reduced pressure in the range between 0.01 to 1000 mbar, more particularly between 1 to 1000 mbar and preferably between 80 to 300 mbar. The solvent or hydrolysis alcohol is removed from the reaction mixture until the composition has a content of volatile solvent, such as hydrolysis alcohol, and any groups hydrolyzable to volatile solvent, such as alkoxy groups, of below 12% by weight to 0% by weight in the overall composition, more particularly below 12% by weight to 0.0001% by weight, preferably below 10% by weight to 0% by weight, more preferably below 5% by weight to 0% by weight, even more preferably below 2% by weight to 0% by weight, to below 1% to 0% by weight. It is particularly preferable for the volatile solvent content of the total composition to be between 0.5% to 0.001% by weight.

Volatile solvents, or groups hydrolyzable to volatile solvents, are to be understood as meaning alcohols, such as methanol, ethanol, isopropanol, n-propanol, and alkoxy groups which hydrolyze to alcohols, acyloxy-containing radicals and also the hydrolysis-derived acetic acid or formic acid, or else aryloxy groups capable of forming phenols and also glycols as well as partially etherified glycols, such as ethylene glycol, diethylene glycol or methoxyethanol, which can either be added to the formulation or are formed by hydrolysis of their silyl esters.

It is particularly preferable for the process of the present invention to utilize a tertiary amine of the general formula II, $$N(R^4)_3 \tag{II}$$

where each $R^4$ independently is a linear, branched and/or cyclic substituted or unsubstituted alkyl group having 1 to 30 carbon atoms, optionally substituted with one or more —$NR^5{}_2$—, —$OR^1$— and/or —$SR^6$ groups, with each $R^1$ being independently hydrogen or $R^4$; $R^6$ is an alkyl or alkenyl group having 1 to 30 carbon atoms; and/or one, two or three $R^4$ groups are each independently $(R^1O)_{3-x}(R^2)_x Si[(R^3)_n CH_2—]$, where $R^1$, $R^2$, $R^3$, x and n are each as defined above, or optionally its hydrolysis and/or condensation products. Advantageously, at least one $R^4$ may comprise at least one oligomeric organofunctional silanol or co-condensate, block co-condensate, more particularly $R^4$ comprises a $(-O_{1/2}-)_{3-x}(R^2)_x Si[(R^3)_n CH_2—]$ radical in an organosilicon compound obtained by condensation.

Alternatively, two $R^4$ groups in the form of $(R^4)_2$ can combine with a heteroatom N, S or O to form cycle or heteroaromatic having 1 to 7 carbon atoms, such as for example but not exclusively pyrrole, pyridine, etc.

Further tertiary amines or amino compounds useful for preparing the quaternary amino-functional organosilicon compound in order that corresponding products may be formed are disclosed hereinbelow.

By way of tertiary amines, more particularly of formula II, it is particularly preferable to use amines having a boiling point above 85° C. and/or particularly amines selected from the following group, such as amines of formula IIa, IIb and/or an amine having a radical of formula IIc and/or of formula IId, for example with IIc or IId as a B group of the silane of general formula III, and/or compounds derived therefrom.

According to the present invention, the tertiary amine of formula II used in the process may likewise advantageously be an amine selected from the formulae IIa and IIb, $$(R^{14})_2N[CH_2CH_2N(R^{14})]_h CH_2CH_2N(R^{14})_2 \tag{IIa},$$

where $R^{14}$ in each occurrence is independently a branched, unbranched and/or cyclic alkyl, aryl, more particularly benzyl, or alkylaryl having 1 to 20 carbon atoms, in this case $R^{14}$ is preferably methyl or ethyl, and more preferably methyl, and h is equal to 0, 1, 2, 3, 4, 5, 6 or 7, more particularly h is equal to 0, 1, 2, 3 or 4; IIa is preferably tetramethylethylenediamine or pentamethyldiethylenetriamine; when $R^{14}$ is methyl ($CH_3$), IIa is $(CH_3)_2N[CH_2CH_2N(CH_3)]_h CH_2CH_2N(CH_3)_2$;

$$[(CH_3)—(CH_2)_w]_{p*}N(R^{14})_{3-p*} \tag{IIb},$$

where w is equal to 2 to 20, more particularly w is equal to 8 to 14, and $R^{14}$ is as defined above, p* is equal to 1 or 2, as particularly in dioctylmethylamine, di-n-nonylmethylamine, di-n-decylmethylamine, di-n-undecylmethylamine, di-n-dodecyl-methylamine, di-n-tridecylmethylamine or di-n-tetradecylmethylamine.

It is particularly preferable to use tertiary amines from the group tetramethylethylenediamine, pentamethylethylenetriamine, tetraethylethylenediamine, penta-ethylethylenetriamine and/or tributylamine or mixtures containing at least two of these amines.

In general, it is also possible to use a cyclic tertiary amine and/or an aromatic amino compound in the present process, as by reaction with N-alkylpyrrole, N-alkylpyrrolidine, N-alkylpiperidine, N-alkylmorpholine, N-alkylimidazole, N-alkylpiperazine, pyridine, pyrazine.

In a further alternative, the tertiary amine of formula II reacted in the process of the present invention can be an aminoalkyl-functional alkoxysilane having a radical of formula IIc or its hydrolysis and/or condensation product; for example—but not exclusively—formula IIc or IIc* can correspond to a group B of formula III:

$$[(CH_3(CH_2)_o]_2N(R^{15})— \tag{IIc}$$

$$[(CH_3(CH_2)_o]_2N(CH_2)_p— \tag{IIc*},$$

where $R^{15}$ is a linear, branched and/or cyclic alkylene, arylene or alkylenearyl group having 1 to 20 carbon atoms, where $0 \leq o \leq 6$ and o is independently=0, 1, 2, 3, 4, 5 or 6 in IIc and/or IIc*; more particularly $R^{15}$ can be a —$(CH_2)_p$—, as depicted in formula IIc*, in which case $0 \leq p \leq 6$ and p is independently=0, 1, 2, 3, 4, 5 or 6, and/or the tertiary amine of formula II can include a radical of formula IId, more particularly formula IId or specifically formula IId* can be a radical of an aminoalkyl-functional alkoxysilane or its hydrolysis and/or condensation product; for example—but not exclusively—formula IId or IId* can also correspond to a group B of formula III:

$$(R^{14})_2N[(CH_2)_g(NH)]_s—(R^{15})— \tag{IId}$$

$$(CH_3(CH_2)_f)_2N[(CH_2)_g(NH)]_s—(CH_2)_i— \tag{IId*}$$

where $R^{14}$ and $R^{15}$ in IId are each independently defined as above and where, in formula IId and/or IId*, $0 \leq g \leq 6$, $0 \leq s \leq 6$, i.e., g and/or s are each independently equal to 0, 1, 2, 3, 4, 5 or 6, and/or, in formula IId*, $R^{14}$ represents a $(CH_3(CH_2)_f$— group and $R^{15}$ represents a —$(CH_2)_i$— group, with $0 \leq f \leq 3$; $0 \leq g \leq 6$, $0 \leq s \leq 6$, $0 \leq i \leq 6$, i.e., f=0, 1 or 2; g, s and/or i are each independently equal to 0, 1, 2, 3, 4, 5 or 6.

Examples of compounds of these tertiary silane-functionalized amines of the general formula II are depicted hereinbelow, wherein the radicals of the compounds are substituted as defined in IIc, IIc* and III:

$$([(CH_3(CH_2)_o]_2N(R^{15})—)_{1+b}Si(R^8)_a(R^7O)_{3-a-b}$$

$$((R^{14})_2N[(CH_2)_g(NH)]_s—(R^{15})—)_{1+b}Si(R^8)_a (R^7O)_{3-a-b}$$

where a is equal to 0, 1 or 2, b is equal to 0, 1 or 2 and (a+b)<3.

Additionally and/or alternatively, the tertiary amine can be an N-alkylpyrrolidine, N-arylpyrrolidine, N-alkylpiperidine, N-alkylmorpholine, N-alkylimidazolidine, N-alkylpiperazine, N,N'-dialkylpiperazine, acridine, phenazine, pyrazine.

Useable tertiary amines are advantageously trimethylamine, triethylamine and/or preferably at least one of the following amines selected from triisopropylamine, tri-n-propylamine, tribenzylamine, dimethylethylamine, dimethyl-n-butylamine, dimethyl-n-hexylamine, diethyl-n-octylamine, dimethyldodecylamine, dimethylpentadecylamine, diethyloctadecylamine, dimethylheptadecylamine, diethyltetradecylamine, dimethylhexacosylamine, methylethylisopropylamine, methylethylbenzylamine, diethyldecylamine, methyldipentylamine, kethylethylheptylamine, methylethylnonylamine, cyclopropyldimethylamine, cyclobutyldiethylamine, cyclopentyldi-n-propylamine, cyclohexyldimethylamine, cyclohexyldiethylamine, cyclohexylmethylethylamine, cycloheptyldimethylamine, cyclooctyldiethylamine, cyclohexyldioctylamine, cyclononyldimethylamine, cyclodecyldiethylamine, cycloundecyldimethylamine, cyclododecyldiethylamine, N-methylpyrrolidine, (=N-methylazolidine under IUPAC Rules), N-ethylpyrrolidine, N-isopropylpyrrolidine, N-benzyl-5-pyrrolidine, N-methylpiperidine, N-ethylpipericine, N-n/isopropylpiperidine, N-benzylpiperidine, N-methylmorpholine or 4-methyltetrahydro-1,4-oxazine, N-ethylmorpholine, N-n-butylmorpholine, N-benzylmorpholine, N-methylimidazolidine, N-ethylimidazolidine, N-n-pentylimidazolidine, N-benzylimidazolidine, N-methylpiperazine, N-ethylpiperazine, N-isopropylpiperazine, N-benzylpiperazine, N-methylthiazolidine, N-ethylthiazolidine, N-methyloxazolidine, N-methyltetrahydro-1,4-thiazine, N-ethyltetrahydro-1,4-thiazine, N-benzyltetrahydro-1,4-thiazine, N-methylperhydroacepine, N-methylhexamethyleneimine, N-ethylperhydroacepine, N-benzylperhydroacepine, N-methylperhydrooxine (=N-methylheptamethyleneimine), N-isopropylperhydrooxine, N-benzylperhydrooxine, N-ethyltetramethyleneimine, N-methylpentamethyleneimine, N-ethylpentamethyleneimine and N-benzylpenta-methyleneimine.

By way of tertiary amines of formula II it is preferably also possible to use the following amino-functional alkoxysilanes having tertiary amino groups, such as, more particularly, tertiary aminoalkoxysilanes, diaminoalkoxysilanes, triaminoalkoxysilanes, bis(triethoxysilylalkyl)amine or tris(triethoxysilylalkyl)amine.

Possible bis(alkoxysilylalkyl)amine compounds include particularly $(OR^{1**})_{b*}R^{2*}_{a*}Si-A-SiR^{2*}_{a*}(OR^{1**})_{b*}$, with a*, b*=0, 1, 2 or 3 and a*+b* equal 3 per Si atom, where $R^{1**}$ and $R^{2*}$ are each independently alkyl having 1 to 24 carbon atoms, preferably methyl, ethyl and/or propyl. With A for a bisaminoalkyl-functional group of formula V, where $N^\#$ in V can correspond to the tertiary nitrogen (N) of formula V, $$—(CH_2)_{i*}—[NR^{16}(CH_2)_{f*}]_{g*}N^\#R^{16}[(CH_2)_{f*}NR^{16}]_{g*}—(CH_2)_{i*}— \quad (V)$$

where $R^{16}$ in each occurrence can be independently a branched, unbranched and/or cyclic alkyl, aryl or alkylaryl group having 1 to 20 carbon atoms, where $R^{16}$ is preferably methyl or ethyl, more preferably methyl, and where in formula V i*, f* or g* are each independently the same or different, with i*=0 to 8, f*=1, 2 or 3, g*=0, 1 or 2 and $R^{1**}$ corresponding to a linear, cyclic and/or branched alkyl radical having 1 to 4 carbon atoms, where i* corresponds particularly to one of the numbers 1, 2, 3 or 4, preferably 3, and $[(H_5C_2O)_3Si(CH_2)_3NCH_3(CH_2)_3Si(OC_2H_5)_3]$ is particularly preferred.

Useful tris(alkoxysilylalkyl)amines, particularly of formula VI, include,

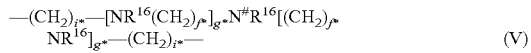

$$N[ZSi(R^{12})_\Omega(OR^{13})_{3-\Omega}]_3 \quad (VI)$$

where Z in each occurrence is independently a bivalent alkylene radical, particularly from the series —$CH_2$—, —$(CH_2)_2$—, —$(CH_2)_3$— or —$[CH_2CH(CH_3)CH_2]$—, $R^{12}$ is a linear, branched and/or cyclic alkyl radical having 1 to 24 carbon atoms, more particularly having 1 to 16 carbon atoms and preferably having 1 to 8 carbon atoms and more preferably having 1 to 4 carbon atoms, or is an aryl radical and independently $\Omega$ is =0 or 1, $R^{13}$ in each occurrence is independently in VIII a linear, cyclic and/or branched alkyl radical having 1 to 24 carbon atoms, more particularly having 1 to 16 carbon atoms, preferably having 1 to 8 carbon atoms, more preferably having 1 to 4 carbon atoms. Preferably, $R^{13}$ is a methyl, ethyl or propyl radical. The nitrogen of formula VIII again corresponds to the nitrogen (N) of the more general formula V and $[ZSi(R^{12})_\Omega(OR^{13})_{3-\Omega}]$ would correspond to an $R^1$. Preference for use as tertiary tris(trialkoxysilane)amine is given to tris(triethoxysilylpropyl)amine or tris(trimethoxysilylpropyl)amine. In general, compounds of formula VI, the hydrolysis and/or condensation products thereof can be used as tertiary amine in the process of the present invention.

The process of the present invention more preferably utilizes a haloalkyl-functional silane of formula I selected from the following group: chloropropyltrimethoxysilane, chloropropyltriethoxysilane, chloropropylmethyldimethoxysilane and chloropropylmethyldiethoxysilane and/or its hydrolysis and/or condensation product.

Further haloalkylsilanes of formula I which are preferably useable in the process of the present invention are, more particularly selected from the group, 3-chloropropyltrimethoxysilane, 3-chloropropyltriethoxysilane, 3-chloropropyl-tripropoxysilane, chloropropylmethyldimethoxysilane, chloropropylmethyldiethoxysilane, chloropropyldimethylethoxysilane, chloropropyldimethylmethoxysilane, chloroethyltrimethoxysilane, chloroethyltriethoxysilane, chloroethylmethyl-dimethoxysilane, chloroethylmethyldiethoxysilane, chloroethyldimethylmethoxysilane, chloroethyldimethylethoxysilane, chloromethyltriethoxysilane, chloromethyl-trimethoxysilane, chloromethylmethyldimethoxysilane, chloromethylmethyldiethoxysilane, chloromethyldimethylmethoxysilane, chloromethyldimethyl-ethoxysilane, 2-chloroisopropyltris(methoxyethoxy)silane, 3-chloropropylcyclo-hexyldiethoxysilane, 3-chloroisobutyltrimethoxysilane, 3-chloroisobutyltriethoxysilane, 3-chloropropylcyclohexyldimethoxysilane, 3-bromoisopropyldiethylcyclohexoxysilane, 3-chloropropylcyclopentyldieneethoxysilane, 3-bromoisobutyltrimethoxysilane, 3-chloroisobutylbis(ethoxyethoxy)methylsilane, 4-bromo-n-butyltriethoxysilane, 4-chloro-n-butyldiethoxycyclopentylsilane, 5-chloro-n-pentyltri-n-butoxysilane, 5-bromo-n-pentyltriethoxysilane, 4-bromo-3-methylbutyldimethoxyphenylsilane, 5-bromo-n-pentyltri-n-butoxysilane, 5-chloro-n-pentyltriethoxysilane, 6-chloro-n-hexylethoxydimethylsilane, 6-bromo-n-hexylpropyldipropoxysilane, 6-chloro-n-hexyldiethoxyethylsilane, 7-chloro-n-heptyltriethoxysilane, 7-chloroheptyldimethoxy-cycloheptylsilane, 7-bromo-n-heptyl-, diethoxycyclooctylsilane, 8-chloro-n-octyltriethoxysilane, 8-bromo-n-octyldimethylcyclohexoxysilane, 3-chloropropyl-diethoxyphenylsilane, 3-chloropropyl-methoxyethoxybenzylsilane, 3-bromopropyl-dimethoxybenzylsilane and/or their hydrolysis and/or homo- and/or co-condensation products or advantageously 1,4-chlorophenyltrimethoxysilane, 1,4-chlorobenzyltriethoxysilane and chloromethyl-p-methylphenyltrimethoxysilane and/or their hydrolysis and/or homo- and/or co-condensation products are used. Particular preference is given to using purely chloroalkyl-substituted alkoxysilanes in the process of the present invention.

In preferred processes, $R^3$ in formula I is a linear, branched and/or cyclic alkylene having 1 to 18 carbon atoms, more particularly a methylene (—$CH_2$—), ethylene [—$(CH_2)_2$—], propylene [—$(CH_2)_3$—], butylene [—$(CH_2)_4$— or —$(CH_2)CH(CH_3)(CH_2)$—] and n=0 with Hal equal chlorine. It is particularly preferable for the grouping —$[(R^3)_nCH_2Hal]$ to be a chloromethylene, chloroethylene, 3-chloropropylene,

2-chloropropylene, 2-chloroisopropylene, chlorobutylene, chloroisobutylene, chloropentyl, chlorohexyl, chlorocyclohexyl, chloroheptyl, chlorooctyl, chloro-n-octyl or chlorocyclooctyl group. Conveniently, the corresponding bromine-substituted groups can also be used for Hal or a grouping —[(R$^2$)$_n$CH$_2$L] with L as leaving group with a sulfonic ester-substituted group (e.g., triflate) or nitric acid or sulfuric ester-substituted groups.

In a particularly preferred process variant, the reaction takes place in the presence of at least one further water-soluble, condensation-capable, organofunctional silicon compound, its hydrolysis, homo-, co-, block co-condensate or mixtures thereof, particularly to form oligomeric/polymeric quaternary aminoalkyl-functional organosilicon compounds by condensation reactions.

This silicon compound, its hydrolysis, homo-, co-, block co-condensate, more particularly monomeric, oligomeric or polymeric silicon compounds, or mixtures thereof, are more particularly derived from at least one compound of formula III and can be added to the process particularly together with a compound of formula I and/or II, as defined above, or after at least single addition of water. The co-condensation of two alkoxysilanes is thereafter shown in idealized form (the R groups may an alkyl or aminoalkyl group, for example—but not exclusively—methyl, ethyl, propyl, butyl, N,N-dimethylaminoethyl):

Co-condensation:

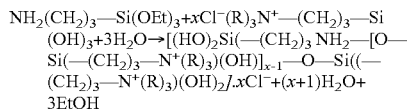

and also

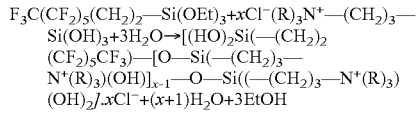

where the condensation/co-condensation can be continued and x can be a number from 1 to ∞.

By way of oligomeric or polymeric silicon compounds there can be used in the process of the present invention as they are for example but not exclusively disclosed, discernible or cited in WO 2006/010666, EP 0 846 717 A1, EP 0846 716 A1, EP 1 101 787 A1, EP 0 960 921 A1, EP 0 716 127 A1, EP 1 205 505 A, EP 0 518 056 A1, EP 0 814 110 A1, EP 1 205 481 A1 and EP 0 675 128 A, the disclosure content of the preceding documents being expressly incorporated herein in full by reference.

For this purpose, component C is suitably additionally used in the process of the present invention, particularly during the reaction, and comprises at least one further organofunctionalized silicon compound of formula III, its hydrolysis products, condensation products or mixtures thereof,

where R$^7$ in each occurrence independently represents hydrogen, a linear, branched and/or cyclic alkyl group having 1 to 8 carbon atoms, aryl, arylalkyl or acyl, preferably alkyl having 1 to 5 carbon atoms, more preferably methyl, ethyl, propyl, R$^8$ in each occurrence independently signifies a linear, branched and/or cyclic alkyl group having 1 to 24 carbon atoms, preferably having 1 to 16 and more preferably having 1 to 8 carbon atoms; aryl, arylalkyl and/or acyl and the B groups are the same or different and B represents an organofunctional group, a is equal to 0, 1 or 2, b is equal to 0, 1 or 2 and a+b<3, in particular the compound of the formula III is selected from compounds with B being equal to —[(R$^{10}$)$_n$R$^9$], where R$^{10}$ represents a linear, branched and/or cyclic alkylene and/or alkenylene having 1 to 18 carbon atoms, n is equal to 0 or 1 and R$^9$ in each occurrence independently signifies a substituted or unsubstituted linear, branched and/or cyclic alkyl group having 1 to 30 carbon atoms which may optionally include one or more —NR$^{3*}_2$, —OR$^{3*}$ and/or —SR$^{3*}$ groups, with R$^{3*}$ representing hydrogen and/or with R$^{3*}$ equal R$^9$ and/or R$^9$ together with a heteroatom N, S or O being a cycle or heteroaromatic having 1 to 7 carbon atoms, B being equal to (R$^{5*}$0)$_{3-x*}$(R$^{6*}$)$_{x*}$Si((R$^{2*}$)CH$_2$—), where R$^{5*}$ in each occurrence independently represents hydrogen, a linear, branched and/or cyclic alkyl group having 1 to 8 carbon atoms or represents aryl, arylalkyl and/or acyl, preferably alkyl having 1 to 5 carbon atoms, particularly preferably methyl, ethyl, propyl, R$^{6*}$ in each occurrence independently signifies a linear, branched and/or cyclic alkyl group having 1 to 24 carbon atoms, in particular having 1 to 16, preferably having 1 to 8 carbon atoms, and/or aryl, arylalkyl and/or acyl, R$^{2*}$ is a linear, branched and/or cyclic alkylene and/or alkenylene having 1 to 18 carbon atoms, preferably an alkylene, and x* is equal to 0, 1 or 2, B is a primary, secondary or tertiary amino-functional radical of the general formulae IIIa or IIIb,

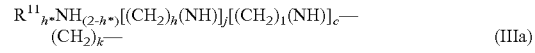 (IIIa)

where 0≤h≤6; h*=0, 1 or 2; j=0, 1 or 2; 0≤l≤6; c=0, 1 or 2; 0≤k≤6 and R$^{11}$ corresponds to a benzyl, aryl, vinyl, formyl radical and/or a linear, branched and/or cyclic alkyl radical having 1 to 8 carbon atoms, preferably k=3, c=1 or 2, l=1, 2 or 3 and j=0, more preferably k=3, c=1 or 2, l=2 for a (2-aminoethylene)-3-aminopropyl radical, or j=0; c=2 and k=3, or else j=1; c=1 and k=3 with h=2, l=2 for a triaminoethylene-3-propyl radical; and in formula IIIb

 (IIIb)

0≤d≤6 and 0≤p≤6, preferably with d equal 1 or 2 and p equal 3,

B is equal to —(CH$_2$)$_{i*}$—[NH(CH$_2$)$_{f*}$]$_{g*}$NH[(CH$_2$)$_{f*}$NH]$_{g*}$—(CH$_2$)$_{i*}$—SiR$^{2*}_{a*}$(OR$^{1**}$)$_{b*}$(IIIc), where i*, f* or g* in formula IIIc are each independently identical or different, with i*=0 to 8, f*=1, 2 or 3, g*=0, 1 or 2 and R$^{1**}$ corresponding to a linear, cyclic and/or branched alkyl radical having 1 to 4 carbon atoms, where i* is more particularly one of the numbers 1, 2, 3 or 4, preferably 3, with a*, b*=0, 1, 2 or 3 and a*+b* equal 3 and R$^{2*}$ an alkyl radical having 1 to 24 carbon atoms, B is a radical R$^{12}$—Y$_q$—(CH$_2$)$_s$—, where R$^{12}$ corresponds to a mono-, oligo- or perfluorinated alkyl radical having 1 to 20 carbon atoms or to a mono-, oligo- or perfluorinated aryl radical, where Y further corresponds to a —CH$_2$—, —O—, -aryl or —S— radical and q is =0 or 1 and s is =0 or 2, more particularly B corresponds to a perfluorinated alkyl radical having 1 to 20 carbon atoms, B is a vinyl, allyl, isopropenyl radical, mercaptoalkyl radical, sulfanealkyl radical, ureidoalkyl radical, acryloyloxyalkyl radical, methacryloyloxyalkyl radical, or a linear, branched or cyclic alkoxy radical having 1 to 24 carbon atoms, more particularly having 1 to 16 carbon atoms and preferably having 1 to 4 carbon atoms, more particularly with a equal 0 and b equal 0, 1 or 2 in formula III for a tetraalkoxysilane, B is a hydroxyalkyl, epoxy and/or ether radical, more particularly a 3-glycidyloxyalkyl, 3-glycidyloxypropyl, dihydroxyalkyl, epoxyalkyl, epoxycycloalkyl, polyalkylglycolalkyl radical or a polyalkylglycol-3-propyl radical, or at least partial hydrolysis and condensation products of one or at least two compounds of formula III.

Preferably, homo-, co- or else block co-condensates of at least two different compounds of formula III can be used as oligomeric or polymeric silicon compounds in the process, as known for example but not exclusively from WO 2006/010666, and also from the aforementioned EP documents.

Preferred compounds of formula III are:
bis(triethoxysilylpropyl)amine [$(H_5C_2O)_3Si(CH_2)_3NH(CH_2)_3Si(OC_2H_5)_3$, bis-AMEO]. Further preferred compounds are: $(H_3CO)_3Si(CH_2)_3NH(CH_2)_3Si(OCH_3)_3$ (bis-AMMO), $(H_3CO)_3Si(CH_2)_3NH(CH_2)_2NH(CH_2)_3Si(OCH_3)_3$ (bis-DAMO), $(H_3CO)_3Si(CH_2)_3NH(CH_2)_2NH(CH_2)_2NH(CH_2)_3Si(OCH_3)_3$ (bis-TRIAMO), bis(diethoxy-methylsilylpropyl)amine, bis(dimethoxymethylsilylpropyl)amine, bis(triethoxysilylmethyl)amine, bis(trimethoxysilylmethyl)amine, bis(diethoxymethylsilylmethyl)amine, bis(dimethoxymethylsilylmethyl)amine, $(H_3CO)_2(CH_3)Si(CH_2)_3NH(CH_2)_2NH(CH_2)_3Si(OCH_3)_2(CH_3)$ and/or $(H_3CO)_3(CH_3)Si(CH_2)_3NH(CH_2)_2NH(CH_2)_2NH(CH_2)_3Si(OCH_3)_2(CH_3)$.

Preferred aminoalkyl-functional silanes of formula III are:
diaminoethylene-3-propyltrimethoxysilane ($H_2N(CH_2)_2NH(CH_2)_3Si(OCH_3)_3$, DAMO);
triaminodiethylene-3-proplytrimethoxysilane $H_2N(CH_2)_2NH(CH_2)_2NH(CH_2)_3Si(OCH_3)_3$ (TRIAMO), (2-aminoethylamino)ethyltriethoxysilane, butyl N-butyl-3-aminopropyltriethoxysilane, N-butyl-3-aminopropylmethyldiethoxysilane, N-butyl-3-aminopropyltrimethoxysilane, N-butyl-3-aminopropylmethyldimethoxysilane, N-butyl-1-aminomethyltriethoxysilane, N-butyl-1-aminomethylmethyldimethoxysilane, N-butyl-1-aminomethyltrimethoxysilane, N-butyl-1-aminomethylmethyltriethoxysilane, N-formyl-3-aminopropyltriethoxysilane, N-formyl-3-aminopropyltrimethoxysilane, N-formyl-1-aminomethylmethyldimethoxysilane and/or N-formyl-1-aminomethylmethyldiethoxysilane, and also the corresponding N-methyl-, N-ethyl-, N-propyl-substituted aminosilanes or mixtures thereof. By way of amino-functionalized silicon compounds there can be used in particular the following, such as bis(3-triethoxysilylpropyl)amine, bis(3-trimethoxysilylpropyl)amine, 3-aminopropylmethyldiethoxysilane, 3-aminopropylmethyldimethoxysilane, 3-aminopropyltriethoxysilane, aminoethyl-N'-2-aminoethyl-N-3-aminopropyltrimethoxysilane, N-(n-butyl)-3-aminopropyltrimethoxysilane, benzyl-2-aminoethyl-3-aminopropyltrimethoxysilane, 2-aminoethyl-3-aminopropylmethyldimethoxysilane, 2-aminoethyl-3-aminopropyltrimethoxysilane, and/or their hydrolysis, homo- and/or co-condensation products and/or mixtures thereof.

By way of organo-functionalized silicon compounds as per component C there can also be used particularly the following, such as phenyltrimethoxysilane, phenyltriethoxysilane, 3-glycidoxypropyltriethoxysilane, 3-glycidoxypropyltrimethoxysilane, tridecafluoroctyltriethoxysilane, ethyl polysilicate, tetraethyl orthosilicate, tetra-n-propyl orthosilicate, 3-mercaptopropyltrimethoxysilane, 3-mercaptopropyltriethoxysilane, 3-methacryloxypropyltrimethoxysilane, 3-methacryloxypropyltriethoxysilane, 3-methacryloxypropylmethyldimethoxysilane, 3-methacryloxypropylmethyldiethoxysilane, 3-ureidopropyltriethoxysilane, 3-ureidopropyltrimethoxysilane, vinyltriethoxysilane, vinyltrimethoxysilane, vinyltris(2-methoxyethoxy)silane, vinylbenzyl-2-aminoethyl-3-aminopropylpolysiloxane optionally in methanol and/or their hydrolysis, homo- and/or co-condensation products and/or mixtures thereof.

It can further be preferable to use metal oxides as further component in the process of the present invention, preferably metal oxides having condensation-capable hydroxyl groups. These are more particularly silica, pyrogenous silicic acid, precipitated silicic acid, silicates, boric acid, titanium dioxide, aluminum oxide, aluminum oxide hydrate, ATH (aluminum trihydroxide, $Al(OH)_3$), magnesium hydroxide ($Mg(OH)_2$), cerium oxide, yttrium oxide, calcium oxide, iron oxide, zirconium oxide, hafnium oxide, boron oxide, gallium oxide, indium oxide, tin oxide, germanium oxide and also corresponding hydroxides and oxide hydrates and also mixtures of at least two of the aforementioned compounds with one another.

To adjust the pH and/or as catalyst, the composition or reaction mixture may have added to it at all times an organic or inorganic acid, for example formic acid, acetic acid, hydrochloric acid or other acids familiar to a person skilled in the art.

It is particularly preferable for the following compounds of formula I, II and of formula III, their hydrolysis and/or condensation products or mixtures thereof to be used and reacted in the inventive process for preparing inventive quaternary amino-functional organosilicon compounds, such as preferably: formula I and II with formula III where the B group corresponds to a radical $—[(R^{10})_nR^9]_{1+b}$; formula I and II with two compounds of formula III with group B equal $—[(R^{10})_nR^9]_{1+b}$, and a further compound of formula III with group B wherein group B corresponds to a primary, secondary and/or tertiary amino-functional group of the general formulae IIIa or IIIb; formula I and II with a compound of formula III where group B corresponds to a radical $R^{12}—Y_q—(CH_2)_s—$; formula I and II with two different compounds of formula III where one B group corresponds to a radical $R^{12}—Y_q—(CH_2)_s—$ and another B group corresponds to a primary, secondary and/or tertiary amino-functional group, more particularly of the general formulae IIIa or IIIb; formula I and II with a compound of formula III wherein group B corresponds to a hydroxyalkyl, epoxy radical, more particularly a 3-glycidyloxyalkyl, 3-glycidyloxypropyl, dihydroxyalkyl, epoxyalkyl, epoxycycloalkyl radical; formula I and II with a tetraalkoxysilane of formula III.

In the process of the present invention, the silane(s) of formula III and/or hydrolysis, homo- and/or co-condensation products thereof can be initially charged together with the chloro-functionalized silane at the start of the process, or be added to a reaction mixture of components A and B at any later time in the course of the process. The addition can preferably take place after the first, second or third addition of water.

More particularly, the process of the present invention can be carried out without use of iodides and substantially without any use of solvents, such as glycols or glycol ethers, i.e., substantially without addition of a solvent. Moreover, it is particularly the aqueous preparation of the organosilicon compounds which forecloses the additional use of hydrosilanes in the process of the present invention.

The process can be carried out with advantage as follows. First, the haloalkyl-functional silane, more particularly a component A, and optionally at least one silane of formula III, i.e., optional component C, are mixed in a suitable reaction vessel; for example a stirred tank reactor with temperature control, metering means and distillation apparatus; with the tertiary amine, more particularly a component B. The temperature here should be below the boiling temperature of the amine used and also below the boiling temperature of the silane used respectively. Preferably, the silane or silane mixture is initially charged and the tertiary amine is rapidly added within a few seconds to minutes. The molar ratio of chloroalkyl function/tertiary amino functions of the compounds can vary in the range from 2:1 to 1:10. When the ratio is 1:1, every chloroalkyl function will react with an amino function. Preferably, the ratio of all amino functions (primary, secondary and tertiary) to the chloroalkyl is about 1:1. When a lower ratio than 1:1 is chosen, unreacted amino functions remain in the composition, which remain in the solution or can be separated off. When the tertiary amine contains more than one tertiary amino function, a ratio lower than 1:1 for tertiary amine to chloroalkyl function can be used in order that all the tertiary amines may be allowed to react with a chloroalkyl function.

In addition, a preferred embodiment of the process of the present invention can be carried out with advantage when
  the components A and B and optionally C are mixed, wherein the mixture may optionally have added to it a diluent medium, preferably an alcohol, more preferably methanol, ethanol, isopropanol,
  water is continuously or discontinuously metered into the mixture in an amount of 0.5 to 500 mol of water per mole of silicon atoms present, preferably under stirring, and optionally a catalyst is added to the reaction mixture,
  the reaction mixture present is set to a temperature between 20 and 150° C. at ambient pressure or reduced pressure, and
  the resultant hydrolysis alcohol is at least partially, preferably essentially completely, removed from the reaction mixture as is any solvent/diluent medium used, and
  the composition thus obtained is optionally diluted with water, wherein the level of active ingredient, i.e., of mixture of quaternary amino-functional organosilicon compounds which is obtained according to the process and which contains at least one oligomerized quaternary amino-functional organosilicon compound, in the composition is preferably adjusted to 0.1% to 99.9% by weight and thereafter optionally admixed or contacted with at least one further component from the series of pigments, fillers, binders, crosslinkers, optical brighteners, thickeners, rheological auxiliaries, coating auxiliaries or some other auxiliary.

When 3-chloropropyltriethoxysilane (CPTEO) is reacted with tetramethylethylenediamine (TMEDA), for example, a ratio of about 1:2 for chloroalkyl functions to tertiary amine functions can be sufficient to achieve full reaction of practically all TMEDA molecules, see example 1. A ratio of >1:1 for the functional groups will leave behind unreacted chloroalkylsilyl functions which, however, can be co-incorporated in the oligomeric end product through hydrolysis of the alkoxysilyl functions and condensation of the silanol functions. When further organofunctional alkoxysilanes are used during hydrolysis and condensation reaction, as per formula III, they will become co-incorporated into the inventive oligomeric product, see in the idealized form formula VII.

This makes it possible to obtain inventive multifunctional oligomeric or polymeric quaternary aminoalkyl-functional organosilicon compounds of formula VII which, in addition to the quaternary amino function, contain further organofunctional groups.

The use, for instance, of alkylalkoxysilanes, e.g., methyl-, propyl-, butyl-, isobutyl-, octyl-, isooctyl- or hexadecyltrialkoxysilanes or -methyldiethoxysilanes or -dimethylalkoxysilanes, can result in the formation of alkylsilyl- and quaternary amino-functional co-condensates. In the same way it can also be used to introduce further organo functions, for example amino, diamino, triamino, mercapto, glycidyloxy, (meth)acryloxy or fluoroalkyl functions, into the oligomeric product.

Diluents, including for example methanol or ethanol, can be used in special cases to adjust the viscosity for example. Preferably, no solvent is used. A diluent can also be used in the subsequent steps, hydrolysis and/or condensation and more particularly distillation for viscosity adjustment and for solubilization. In the course of the distillation step, the diluent is removed again according to the present invention.

The mixing operation is preferably carried out as rapidly as possible. This is followed by the addition of water, particularly in an amount between 0.5 mol of water per mol of Si to 500 mol of water per mol of Si. The water is added under agitation within a period between 1 min and 10 hours, preferably within 10 min to 1 hour. The reaction mixture/solution usually becomes cloudy in the process. It is stirred and heated, particularly between 10° C. to the reflux temperature, depending on the inputs used, the reaction is preferably carried out at 20 to 150° C. and more preferably below 100° C., until a clear solution has formed.

It is preferable to maintain a postreaction period under reflux, particularly in the aforementioned temperature range, of 30 minutes to 24 h and preferably between 1 h to 8 h. Further water can be added during this period. This is followed by distillative removal of hydrolysis alcohols and any solvents added. The distillatively removed amount is preferably replaced with equal parts of water. This can be done by continuous addition or by addition in sub-steps. It is preferable for the addition to take place in sub-steps wherein the rate of addition is preferably set as high as possible.

The distillation preferably takes place under reduced pressure, more particularly between 0.01 mbar to 1000 mbar, more particularly between 1 to 1000 mbar and more preferably between 80 to 300 mbar. Distillation is preferably carried on until only water is detectable at the top of the separation column. Distillatively removed water is replenished by renewed addition of water. At the end of the distillation, the desired final concentration for the solution can be set by adding further water.

The present invention accordingly also provides oligomeric/polymeric quaternary aminoalkyl-functional organosilicon compounds and also their mixtures obtainable by the process of the present invention.

The present invention further provides a composition containing quaternary aminoalkyl-functional organosilicon compounds and water, obtainable by the process of the present invention.

The level of inventively quaternary amino-functional organosilicon compound, more particularly of formula VII, in subject compositions can be set as desired in a range between 0.001% to 99.5% by weight and preferably between 0.1% by weight to 90% by weight, in the overall composition.

Compositions according to the present invention are preferably marked by a content of active ingredient, i.e., quaternary amino-functional organosilicon compounds obtained according to the process, the composition containing at least one oligomerized quaternary amino-functional organosilicon compound, in the composition ranging from 0.1% to 99.9% by weight, preferably 0.5% to 90% by weight, more preferably 5% to 70% by weight, even more preferably 7% to 60% by weight and more particularly 10% to 50% by weight, wherein all the constituents in the composition sum to 100% by weight.

Compositions according to the present invention are further marked by a water content in the range from 0.0999 to 99.9% by weight, and are advantageously thinnable with water in practically any proportion: these can also have a level of volatile solvent/hydrolysis alcohol in the overall composition of below 12% by weight to 0% by weight, preferably below 5% to 0.0001% by weight, wherein all the constituents in the composition sum to 100% by weight.

The VOC content of the composition, as defined above, is thus advantageously less than 12% by weight in the overall composition and more preferably below 2% to 0% by weight.

In addition, compositions according to the present invention may contain at least one further of the following components from the series pigments, fillers, binders, crosslinkers, optical brighteners, coating auxiliaries or other auxiliaries.

Compositions according to the present invention also advantageously have a viscosity of <1500 mPa s, preferably ≤1000 mPa s and more preferably 10 to 600 mPa s, more particularly of 100 to 300 mPa s.

The end product obtained according to the present invention, or the composition according to the present invention, is generally liquid and minimally to slightly viscose in that the viscosity is more particularly below 1500 mPa s to 0.001 mPa s, preferably between 1000 and 1 mPa s, more preferably below 300 mPa s, even more preferably below 200 mPa s, yet even more preferably below 100 mPa s, still yet even more preferably between 100 mPa s and 1 mPa s, preference being further given to ranges from 200 to 1 mPa s and more particularly from 100 to 10 mPa s (the viscosity is determined in accordance with DIN 53015).

Moreover, a composition or silane product solution obtained according to the present invention can be as required filtered in a conventional manner in the event of cloudiness.

A preferred use for the compositions of the present invention is the production of papercoating slips. For this it is suitable for an aqueous silica dispersion to be prepared first and treated with the silane system of the present invention, usually under high shearing forces applied using dispersing equipment customary in the industry. The silanized silica dispersion obtained is advantageously marked by a high solids content, high storage stability and low sedimentation tendency. Preferably, the silanized silica dispersion has binder, preferably polyvinyl alcohol, and crosslinker, preferably boric acid, added to it in a second step to produce the papercoating slip, which is very useful for producing photographic grade inkjet papers.

Particular preference is given to a papercoating slip viscosity of preferably below 600 mPa s, more preferably below 450 mPa s, even more preferably below 200 mPa s and more particularly in the range from 2 to 150 mPa s, as in the case of the conditions chosen in example 9. The lower the solids content of the formulation, the lower the capacity of the coating rigs operated therewith, since the volatile constituents of the papercoating slips (mainly water here) generally have to be removed thermally. The higher the solids content of the formulation, the lower the amount of water which has to be removed and the higher the rate of speed at which the coating rigs can be operated. A solids content of >15% by weight is desired for papercoating slips under the conditions chosen in example 9.

Before use, the compositions according to the present invention and also the end products according to the present invention can if required be advantageously thinned with water or other solvents or else mixtures thereof to a content between 10% to 0.01% by weight and preferably to a range from 5% to 0.1% by weight.

Thus, in addition to water, a composition according to the present invention may contain a quaternary aminoalkyl-functional organosilicon compound of formula VII or mixtures thereof, more particularly oligomeric or polymeric and optionally monomeric compounds of formula VII or mixtures thereof,

where $R^{1*}$ and $R^*$ each independently correspond to identical or different organofunctional groups, optionally two $R^*$ radicals combine with N to form a cycle which are connected via a carbon atom to the quaternary nitrogen (N), and at least $R^{1*}$, optionally also $R^*$, comprises an Si atom; preferably the $R^*$ and/or $R^{1*}$ radicals independently comprise a —$CH_2$—Si group; wherein the nitrogen is a cation and Z is an anion; more particularly formula VII is a quaternary alkylammonium-functional organosilicon compound, more particularly Z is a chloride, bromide, acetate, formate, and preferably $R^{1*}$ in formula VII is a $(R^1O)_{3-x-y}(R^2)_n Si[(R^3)_n CH_2$— radical, with $R^1$ hydrogen and/or $R^{1*}$ a hydrolysis or oligomeric or polymeric condensation product of this silyl radical.

According to the present invention, the subject composition is essentially free of volatile solvents, preferably of hydrolysis alcohol, and no longer releases any hydrolysis alcohol at crosslinking in particular.

The present invention also provides an aqueous composition comprising quaternary aminoalkyl-functional organosilicon compounds according to the present invention, obtainable according to at least one of claims 1 to 15. It is particularly preferable for the composition containing quaternary aminoalkyl-functional organosilicon compounds to be obtainable according to a process of claims 1 to 15 by reacting the compounds of formulae I and II, as defined above, optionally in the presence of at least one compound of formula III, as defined above, hydrolysis, condensation products or mixtures thereof, in the presence of 0.5 to 500 mol of water and distillative removal of at least some of the hydrolysis alcohol. Preferably, the composition of the present invention is essentially free of organic solvents and releases essentially no alcohol at crosslinking, and more particularly it has a flashpoint above 90° C.

The invention likewise provides a composition containing quaternary aminoalkyl-functional organosilicon compounds and water, wherein the composition contains quaternary aminoalkyl-functional organosilicon oligomeric and polymeric and optionally monomeric compounds having at least one quaternary aminoalkyl-functional group of the general formula VII or mixtures thereof,

where $R^{1*}$ and $R^*$ each independently correspond to identical or different organofunctional groups, optionally two $R^*$ radicals combine with N to form a cycle which are connected via a carbon atom to the quaternary nitrogen (N), and at least $R^{1*}$, optionally also $R^*$, comprises an Si atom; preferably the $R^*$ and/or $R^{1*}$ radicals independently comprise a —$CH_2$—Si group; wherein the nitrogen is a cation and Z is an anion; more particularly formula VII is a quaternary alkylammonium-functional organosilicon compound, more particularly Z is a chloride, bromide, acetate, formate, and preferably $R^{1*}$ in formula VII is a $(R^1O)_{3-x-y}(R^2)_x Si[(R^3)_n CH_2-$ radical, with $R^1$ hydrogen and/or $R^{1*}$ a hydrolysis or oligomeric or polymeric condensation product of this radical;
and wherein the quaternary aminoalkyl-functional organosilicon compounds of formula VII or mixtures thereof are obtainable from a quaternization reaction and optionally at least partial hydrolysis and/or condensation
of at least one haloalkyl-functional silane of formula I and optionally its hydrolysis and/or condensation products $$(R^1O)_{3-x-y}(R^2)_x Si[(R^3)_n CH_2 Hal]_{1+y} \quad (I)$$

where $R^3$ corresponds to a linear, branched and/or cyclic alkylene and/or alkenylene having 1 to 18 carbon atoms, preferably an alkylene, n is 0 or 1, Hal is chlorine or bromine, preferably chlorine, $R^1$ in each occurrence is independently hydrogen, a linear, branched and/or cyclic alkyl group having 1 to 8 carbon atoms, aryl, arylalkyl and/or acyl, more preferably alkyl having 1 to 5 carbon atoms, preferably methyl, ethyl, propyl and $R^2$ in each occurrence is independently a linear, branched and/or cyclic alkyl group having 1 to 24 carbon atoms, more particularly having 1 to 16 carbon atoms and preferably having 1 to 8 carbon atoms, or aryl, arylalkyl and/or acyl, x is 0, 1 or 2, y is 0, 1 or 2 and x+y is <3,
with a tertiary amine of the general formula II, $$N(R^4)_3 \quad (II)$$

where $R^4$ independently corresponds to organofunctional groups which are connected by a C atom to the tertiary nitrogen (N), optionally two $R^4$ radicals combine with N to form a cycle, more particularly $R^4$ is a linear, branched and/or cyclic substituted or unsubstituted alkyl group having 1 to 30 carbon atoms optionally with one or more $-NR^5_2$, $-OR^1$ and/or $-SR^6$ groups, with $R^6$ in each occurrence independently hydrogen or $R^4$; and/or one, two or three $R^4$ radicals correspond to $(R^1O)_{3-x}(R^2)_x Si((R^3)_n CH_2-)$ and optionally its hydrolysis and/or condensation product, in the presence of a defined amount of water, optionally in the presence of a catalyst, followed by an at least partial removal of the hydrolysis alcohol formed and further addition of water.

The defined amount of water added is preferably in the range from 0.5 to 500 mol of water per mol of silicon atoms, more particularly in the range from 5 to 25 mol of water per mol of silicon atoms, preferably in the range from 10 to 20 mol of water per mol of silicon atoms and more preferably in the range from 12 to 17 mol of water per mol of silicon atoms.

In idealized form, the quaternization reaction and partial hydrolysis may give rise to for example the following compound of formula VII:

$$(R^1O)_3 Si[(R^3)_n CH_2 HaI] \quad + \quad (I)$$

$$(R^{14})_2 N[CH_2 CH_2 N(R^{14})] CH_2 CH_2 N(R^{14})_2 \quad \longrightarrow \quad (IIa)$$

$$[(R^1O)_3 Si[(R^3)_n CH_2 - N^+(R^{14})_2 [CH_2 CH_2 N^*(R^{14})] CH_2 CH_2 N(R^{14})_2] Cl^- \quad (VIIa)$$

or with formation of a quaternary nitrogen atom at the position characterized with an (N*) and/or preferably corresponding hydrolysis and also condensation products (cf. formulae VIIc and VIId).

$$[(R^1O)_3 Si[(R^3)_n CH_2 - N^+(R^{14})_2 [CH_2 CH_2 N^*(R^{14})] CH_2 CH_2 N(R^{14})_2] Cl^- + 3H_2O \longrightarrow$$
$$(VIIa)$$
$$[(HO)_3 Si[(R^3)_n CH_2 - N^+(R^{14})_2 [CH_2 CH_2 N^*(R^{14})] CH_2 CH_2 N(R^{14})_2] Cl^- + 3R^1OH$$
$$(VIIc)$$
$$x[(HO)_3 Si[(R^3)_n CH_2 - N^+(R^{14})_2 [CH_2 CH_2 N^*(R^{14})] CH_2 CH_2 N(R^{14})_2] Cl^- \longrightarrow$$
$$[[O_{1.5} Si[(R^3)_n CH_2 - N^+(R^{14})_2 [CH_2 CH_2 N^*(R^{14})] CH_2 CH_2 N(R^{14})_2] Cl^-]_x + 1.5x\, H_2O$$
$$(VIId)$$

Here x can formally be a number from 1 to ∞ provided $H_2O$ is completely removed from the system.

Moreover, in accordance with chemical understanding, compounds of formulae I and IIb may further give rise to compounds within the meaning of the idealized formula VII:

$$(R^1O)_3 Si[(R^3)_n CH_2 HaI] \quad + \quad (I)$$

$$((CH_3)-(CH_2)_w)_{p*} N(R^{14})_{3-p*} \quad \longrightarrow \quad (IIb)$$

$$[(R^1O)_3 Si[(R^3)_n CH_2 - N^+((CH_2)_w - (CH_3))_{p*} (R^{14})_{3-p*}] Cl^- \quad (VIIb)$$

It is particularly preferable here for the hydrolysis alcohol to be removed essentially completely, more particularly by distillation optionally under reduced pressure. A composition deemed essentially free of volatile solvent, more particularly hydrolysis alcohol, has a solvent content below 12% by weight to 0% by weight in the overall composition, preferably below 12% to 0.0001% by weight, more particularly below 10% by weight to 0% by weight, more preferably below 5% by weight to 0% by weight, even more preferably between 2% to 0% by weight, preferably between 1% to 0% by weight and more preferably between 0.5% to 0.001% by weight.

Preferred compositions are obtainable by adding at least one organofunctional silicon compound of formula III, as defined above, hydrolysis or condensation products or mixtures thereof, before, during or after the reaction of compounds of formula I and II. The organofunctional silicon compounds which can be used are described in detail above.

Preferably, the composition of the present invention is essentially free of organic solvents and releases essentially no alcohol at crosslinking, and more particularly it has a flashpoint above 90° C.

Furthermore, the compositions obtainable by the process of the present invention have a viscosity of below 1500 mPa s to 0.001 mPa s, more particularly below 300 mPa s, preferably below 100 mPa s, more preferably between 1000 and 1 mPa s. Preferred ranges are 200 to 100 mPa s, 100 to 0.01 mPa s, 100 to 20 mPa s or else 10 to 20 mPa s, although which is the preferred range in a particular instance depends on the specific use.

In an aqueous composition according to the present invention, the content, more particularly solids content, of quaternary aminoalkyl-functional organosilicon compounds or a mixture thereof can advantageously be from 0.001% to around 99.5% by weight (including all numerical values therebetween), based on the overall composition. The content can be set directly in the process of the present invention or else be thinned by the user, for example with water, to any desired concentration, for example to from 0.0001% to 2% by weight in the composition. Specifically preferred contents of the compounds, such as the solids content, are more particularly between 0.1% to 90% by weight, preferably 5% to 70% by weight, more preferably 10% to 50% by weight, or preferably between 40% to 65% by weight. The compositions of the present invention are advantageously marked by a low viscosity coupled with a simultaneously high solids content, as evidenced by the exemplary embodiments. This combination of low viscosity and high solids content is a necessary prerequisite for a high capacity in the production of coatings. At the same time, the compositions of the present invention are essentially VOC-free, i.e., they are essentially free of hydrolysis alcohol and release no alcohol at crosslinking. Thus, the compositions of the present invention have a distinctly better performance than known compositions.

The claimed compositions are essentially stable in storage. That is, they do not exhibit any visible changes such as cloudiness or sedimentation or gelling within two weeks, preferably 3 months, more preferably 1 year.

The invention also provides a formulation comprising a composition according to the present invention which comprises at least one of the following components from the series pigments, binders, crosslinkers, optical brighteners, coating auxiliaries, active ingredient and/or auxiliary and/or filler.

The compositions of the present invention are also very useful in inkjet coatings, more particularly for high gloss coats on paper.

A detailed description of this use is given in the cocurrent invention report "Hydrosils with quaternary aminofunction for silica dispersions in IJP application". The production of papercoating slips based on a composition according to the present invention is described in example 9d.

The composition according to the present invention may be used by applying it to a substrate by dipping, spreading, rubbing, spraying, more particularly with droplet sizes below 200 μm, preferably below 100 μm down into the nanometer range; depositing, spincoating or any other technique known to a person skilled in the art. To this end, the composition is adjusted to an organosilicon compound concentration suitable for the method used. Depending on the processing method, therefore, the concentration of organosilicon compound in the composition can be in the range from 0.01% by weight to 99.5% by weight. The methods of application are well known to a person skilled in the pertinent art. In addition, a coating applied to a substrate can cure/bind to the substrate in a conventional manner under ambient conditions and/or via an additionally thermal and/or photochemical treatment. In this way, a composition according to the present invention can be used to treat organic or inorganic substrates, or as an input component in formulations, for example.

Inventive compositions or formulations which are based on an inventive composition are advantageously used for modification, treatment and/or production of substrates, articles, organic or inorganic materials, composite materials, papercoating slips, inkjet applications, papercoating materials, textiles, fillers; in biocidally, antibacterially, fungicidally, algicidally and/or virucidally acting formulations and/or coatings, for finishing of fiber materials, yarns and/or textiles, for textile impregnation, for antistatisization of surfaces, more particularly sheetlike, fibrous, woven, granular and/or pulverulent materials, e.g., wood surfaces, mineral surfaces, glass surfaces, ceramic surfaces, metal surfaces, plastics surfaces, porous mineral building materials, fiber materials, for example textile fibers; or for anti-fingerprint or anticorrosion coating of materials and metals and also pretreated metals. Further fields of use comprise an antistatic finishing of surfaces, e.g., of plastics, glass, ceramic, wood, lacquered surfaces, fiber materials such as glass fibers, mineral wool, carbon fibers, ceramic fibers or textile fibers (inc. fabrics produced from these fibers) and also mineral fillers for example silica, precipitated silicic acid, pyrogenous silicic acid, quartz, calcium carbonate, gypsum, ATH, alpha and gamma $Al_2O_3$, magnesium hydroxide/oxide, iron oxides, clay minerals, sheet-silicates or further fillers familiar to a person skilled in the art.

The products of the present invention can further be used for modification of fillers optionally in combination with other organofunctional silanes or hydrosilane, for example in order that a better dispersibility may be achieved.

Particular preference is given to the use of a composition in papercoating slips, more particularly for inkjet applications, for production of papercoating materials, as papercoating materials, for finishing of fiber materials and/or textiles, for textile impregnation or for modification of fillers. Further preferred use is the coating of filters, tubes, fittings, medical devices or instruments, in swimming pool paints, for coating tiles or surfaces which are in constant contact with moisture or water, as in swimming pools, baths, bathroom ceramics, kitchen ceramics, an exterior skin of buildings, such as exteriors, roof coverings, garden furniture, accessories in the marine sector, ropes, sail cloth, ship exterior skin, etc. and also further applications known to the skilled person pertinent here where problems are known to occur with microorganisms, or else of glass, windows, autoglass, mirrors, optical glasses, surgical instruments, or constituent parts of surgical instruments and microinvasive surgical instruments, endoscopes or parts thereof, canulas, medical hoses, medical apparatus and/or parts thereof, implants, prostheses, stents, gravestones, or of fibers, such as natural fibers and/or artificial fibers, such as, more particularly, cotton, hemp, wool, silk, polyester, acetates, and further materials familiar to the pertinent skilled person. Particular preference is given to the use in wound coverings or else hygiene articles, such as plasters, gauze dressings, diapers, pads and also further medical or hygiene articles familiar to the pertinent skilled person. The coating here can range in size from large areas down into the micro- to nanometer region.

The present invention thus likewise further provides for the use of a composition produced/obtainable according to the present invention for modification, treatment and/or production of formulations, substrates, articles, organic or inorganic materials, composite materials, papercoating slips, inkjet applications, papercoating materials, textiles, fillers, biocidally, fungicidally and/or virucidally acting formulations, for finishing of fiber materials, yarns and/or textiles, for textile impregnation, for antistatisization of surfaces, more particularly sheetlike, fibrous, woven, granular and/or pulverulent materials.

The examples which follow more particularly elucidate the present invention, more particularly the process of the present invention and also the compositions of the present invention, without restricting the invention to these examples.

EXAMPLES

Methods of Determination

Hydrolyzable chloride was titrated potentiographically with silver nitrate (for example Metrohm, type 682 silver rod as indicator electrode and Ag/AgCl reference electrode or another suitable reference electrode). Total chloride content after Wurtzschmitt digestion. For this purpose, the sample is digested with sodium peroxide in a Wurtzschmitt bomb. After acidification with nitric acid, chloride is measured potentiographically with silver nitrate, as above.

In a complete reaction of the chloroalkyl function with tertiary amines, the analytical values for hydrolyzable chloride and total chloride are identical and therefore a measure of the completeness of the reaction, since the sum total of salt-like chloride (amine hydrochloride) and covalently bonded chlorine (chloroalkyl function) is determined by total chloride and exclusively salt like chloride or chloride which can be eliminated with water (amine hydrochloride in the present case) is determined by hydrolyzable chloride. At the beginning of the reaction, the value of hydrolyzable chloride is zero and increases at complete conversion to the value which is measured for total chloride. Therefore, these analyses are very useful in addition to $^1$H and $^{13}$C NMR spectroscopy for reaction policing.

The alcohol content after hydrolysis is determined by gas chromatography. For this purpose, a sample of a defined quantity is hydrolyzed with sulfuric acid (5 g of sample, 25 ml of $H_2SO_4$, w=20%). 75 ml of distilled water are added. Thereafter, neutralization is effected with aqueous sodium hydroxide solution and a steam distillation is carried out. Internal standard 2-butanol. Nitrogen determination, organically bound, ammonium etc. Organically bound nitrogen can be converted into ammonium via Kjeldahl digestion and, after addition of aqueous sodium hydroxide solution, be determined acidimetrically as ammonia (see also DIN 1310, DIN 32625, DIN 32630, DIN EN 25663-H11, DIN 38409-H12, AN-GAA 0629—Büchi 322/343). Determination of $SiO_2$ is done after decomposition with sulfuric acid and Kjeldahl catalyst by determining the weight of precipitated $SiO_2$.

The viscosity is generally determined to DIN 53015.

The determination of the solids content, i.e., of the non-volatile fractions in aqueous and solvent-containing preparations, can be carried out in line with DIN/EN ISO 3251 (Determination of the Non-Volatile-Matter Content of Paints, Varnishes and Binders for Paints and Varnishes) as follows (QM-AA Quality Management Operating Instruction as per German Accreditation Body for Chemistry):

Test instruments—Thermometer (reading accuracy 2 K)
   Disposable dishes of aluminum (d=ca. 65 mm, h=ca. 17 mm)
   Analytical balance (accuracy 1 mg)
   Drying cabinet to 250° C.
   Desiccator A sample is heated to a specified temperature (e.g., 125° C.) in order to remove the volatile fractions of the sample in this way. The solids content is the dry residue of the sample after the heat treatment.

About 1 g of sample is weighed with an accuracy of 1 mg into a disposable dish on an analytical balance. The product must be uniformly distributed in the disposable dish by brief swirling. The dish is stored in a drying cabinet at about 125° C. for 1 h. On completion of the drying operation, the dish is cooled down to room temperature in a desiccator for 20 min and reweighed on the analytical balance accurately to 1 mg. At least 2 determinations must be carried out per test.

$$\text{Solids content}(\%) = \frac{\text{final weight}(g)}{\text{Original weight}(g)} \times 100$$

Solids content —Percentage ratio of sample mass before and after treatment.
Final weight—The sample mass after treatment.
Original weight—The sample mass before treatment.

Example 1

Waterborne VOC-Free Solution of a Quaternary Silane System Prepared from 3-chloropropyltriethoxysilane (CPTEO) and tetramethylethylenediamine (TMEDA)

Apparatus: stirred reactor with distilling device, pot thermometer, top thermometer, vacuum pump, manometer and metering device.

Materials Used:

| Inputs | M (input) [g] | N (inputs) [mol] | w (inputs) [%] | Comment |
|---|---|---|---|---|
| Chloropropyltriethoxysilane | 3206.2 | 13.31 | 37.3 | M = 240.8 g/mol |
| N,N,N'N'-tetramethylethylenediamine | 1547.2 | 13.31 | 18.0 | M = 116.21 g/mol |
| Completely ion-free water: | | | | |
| 1st addition | 1603.1 | | 18.6 | |
| 2nd addition | 641.3 | | 7.5 | |
| 3rd addition | 1600.0 | | 18.6 | |
| Σ (inputs) | 8597.8 | | | | m (ethanol ex hydrolysis) = 1836.8 g;
final weight of product after filtration: 6521.4 g (theory: 6761.1 g);
final weight of distillate: 2946.5 g Procedure:
1. Reaction (duration about 9.7 h): Chloropropyltriethoxysilane is initially charged and tetramethylethylenediamine is rapidly added with stirring. This is followed by the 1st addition of water within about 20 minutes (volume stream about 4.8 l/h) under vigorous stirring. The pot contents are distinctly cloudy and then heated under reflux (about 87° C.) for 6 h. The 2nd addition of water is then made during 10 minutes into the now clarified pot contents (volume stream about 3.9 l/h). After a further 1.5 h of heating under reflux, the 3rd addition of water is made with stirring (during about 20 minutes, volume stream about 4.8 l/h).
2. Distillation (duration about 9 h): At a pot temperature of 49° C. to 54° C., hydrolysis ethanol is distilled off under reduced pressure (100-270 mbar). After about 1700 g of ethanol-water mixture have been distilled off, 327 g of water are rapidly added. To distill off the hydrolysis alcohol almost completely, an at least 60% excess (based on the mass of hydrolysis ethanol) has to be distilled off. The distillatively removed amount of water is returned at the end of the distillation.

3. Filtration (duration about 1 h): Thereafter, the slightly cloudy yellowish product is filtered via pressure filter (2 l) and Seitz 500 depth filter at 0.8 bar overpressure (filtration performance at $d_{filter}$=14 cm: 18 l/h). A slightly yellowish clear liquid is obtained.

Analyses:

| Determination | Result | Theory | Method |
|---|---|---|---|
| Viscosity (20° C.) [mPa s] | 70 | | DIN 53015 |
| Density (20° C.) [g/ml] | 1.107 | | DIN 51757 |
| Refractive index (20° C.) | 1.4224 | | DIN 51423 |
| Color [mg Pt—Co/l] | 75 | | |
| Solids [%] | 48.4 | | DIN 38409-1 |
| pH | 8.6 | | 1:1 in water, DIN 38404-C5 |
| SiO$_2$ [%] | 11.8 | 11.8 | see above |
| Ethanol after hydrolysis [%] | 0.5 | | see above |
| Total N [%] | 5.0 | 5.5 | see above |
| Total chloride [%] | 7.2 | 7.0 | see above |
| Hydrol. chloride [%] | 7.1 | 7.0 | see above |

NMR: $^{13}$C-NMR: about 15% of TMEDA groups are in bisadduct form. 8 mol % of free TMEDA is present per 100 SiCH$_2$ groups.
$^{29}$Si-NMR: 2.5 Si % of silane; 14.6 Si % of M-structures; 49.7 Si % of D-structures; 33.3 Si % of T-structures Example 2

Waterborne VOC-Free Solution of a Quaternary Silane System Prepared from 3-chloropropyltriethoxysilane and tetramethylethylenediamine with Excess of tetramethylethylenediamine Apparatus: stirred reactor with distilling device, pot thermometer, top thermometer, vacuum pump, manometer and metering device.

Materials Used:

| Inputs | m (input) [g] | n (inputs) [mol] | w (inputs) [%] | Comment |
|---|---|---|---|---|
| Chloropropyltriethoxysilane | 401.19 | 1.67 | 36.37 | M = 240.8 g/mol |
| N,N,N',N'-tetramethylethylenediamine | 221.53 | 1.91 | 20.09 | M = 116.21 g/mol |
| Completely ion-free water: | | | | |
| 1st addition | 200.27 | | 18.16 | |
| 2nd addition | 79.82 | | 7.24 | |
| 3rd addition | 200.14 | | 18.15 | |
| Σ inputs | 1102.95 | | | | m (ethanol ex hydrolysis) = 229.4 g;
final weight of product: 859.24 g,
theory: 873.55 g;
final weight of distillate: 1073.13 g Procedure:

1. Reaction (duration about 9.7 h): Chloropropyltriethoxysilane is initially charged and tetramethylethylenediamine is rapidly added with stirring. This is followed by the 1st addition of water within about 20 minutes (volume stream about 4.8 l/h) under vigorous stirring. The pot contents are distinctly cloudy and then heated under reflux (about 84-92° C.) for 6 h. The 2nd addition of water is then made into the now clarified pot contents. After a further 1.5 h of heating under reflux, the 3rd addition of water is made with stirring during about 20 minutes, (volume stream about 4.8 l/h).

2. Distillation: At a pot temperature of 48° C. to 53° C., then, the hydrolysis ethanol and the excess TMEDA are distilled off under reduced pressure (100-270 mbar). During the distillation, a total 859.02 g of water are returned. A clear low-viscosity liquid is obtained.

Analyses:

| Determination | Result | Theory | Method |
|---|---|---|---|
| Viscosity (20° C.) [mPa s] | 43.8 | | DIN 53015 |
| Density (20° C.) [g/ml] | 1.104 | | DIN 51757 |
| Refractive index (20° C.) | 1.4184 | | DIN 51423 |
| Color [mg Pt—Co/l] | 70 | | ISO 6271 |
| Solids [%] | 48.3 | | DIN 38409-1 |
| pH | 8.2 | | 1:1 in water, DIN 38404-C5 |
| SiO$_2$ [%] | 11.6 | 11.4 | see above |
| Ethanol after hydrolysis [%] | <0.1 | | see above |
| Total N [%] | 4.6 | 6.1 | see above |
| Total chloride [%] | 7.0 | 6.8 | see above |
| Hydrol. chloride [%] | 7.0 | 6.8 | see above |

NMR: $^1$H and $^{13}$C NMR spectra show the target product (the silane is in a hydrolyzed and oligomerized state) as the main component (about 75% of the silane used): The formula hereinbelow is an idealized empirical formula of the resulting solid on complete removal of the solvent water and of the water formed by condensation. [(CH$_3$)$_2$N—CH$_2$—CH$_2$—N$^+$(CH$_3$)$_2$CH$_2$—CH$_2$—CH$_2$—SiO$_{1.5}$]$_n$ where n can formally be a number from 1 to ∞, preferably 4 to ∞.

In an aqueous solution, the polymeric product has silanol groups as well as siloxane units.

In addition, small amounts of unconverted TMEDA and secondary signals are observed. There are no pointers to CPTEO. Presumably, small amounts of TMEDA which is reacted 2 times are also present.

The $^{29}$Si NMR spectrum shows: about 2 Si % of silanol (xOH), about 14 Si % of M-structures, about 51 Si % of D-structures, about 33 Si % of T-structures.

Example 3

Waterborne VOC-Free Solution of a Quaternary Silane System Prepared from 3-chloropropyltriethoxysilane and tetramethylethylenediamine with Excess of 3-chloropropyltriethoxysilane Apparatus: stirred reactor with distilling device, pot thermometer, top thermometer, vacuum pump, manometer and metering device.

Materials Used:

| Inputs | m (input) [g] | n (inputs) [mol] | w (inputs) [%] | Comment |
|---|---|---|---|---|
| Chloropropyltriethoxysilane | 401.68 | 1.67 | 38.32 | M = 240.8 g/mol |
| N,N,N',N'-tetramethylethylenediamine | 164.53 | 1.42 | 15.70 | M = 116.21 g/mol |

-continued

| Inputs | m (input) [g] | n (inputs) [mol] | w (inputs) [%] | Comment |
|---|---|---|---|---|
| Completely ion-free water: | | | | |
| 1st addition | 201.45 | | 19.22 | |
| 2nd addition | 80.15 | | 7.65 | |
| 3rd addition | 200.43 | | 19.12 | |
| Σ inputs | 1048.24 | | | | m (ethanol ex hydrolysis) = 229.4 g;
final weight of product after filtration: 771.70 g,
theory: 818.84 g;
final weight of distillate: 377.65 g Procedure:
1. Reaction (duration about 9.7 h): Chloropropyltriethoxysilane is initially charged and tetramethylethylenediamine is rapidly added with stirring. This is followed by the 1st addition of water within about 18 minutes under vigorous stirring. The pot contents are distinctly cloudy and then heated under reflux (about 82-84° C.) for 6 h. The 2nd addition of water is then made during 9 minutes into the now clarified pot contents. After a further 1.6 h of heating under reflux, the 3rd addition of water is made with stirring, during about 13 minutes.
2. Distillation: At a pot temperature of 52° C. to 60° C., then, the hydrolysis ethanol is distilled off under reduced pressure (100-270 mbar). During the distillation, a total 859.02 g of water are returned.
3. Filtration: Thereafter, the slightly cloudy yellowish product is filtered via pressure filter and Seitz K800. The resulting slightly cloudy liquid is again filtered through a K700 filter. This gives a clear slightly yellowish fluid.

Analyses:

| Determination | Result | Theory | Method |
|---|---|---|---|
| Viscosity (20° C.) [mPa s] | 88.2 | | DIN 53015 |
| Density (20° C.) [g/ml] | 1.114 | | DIN 51757 |
| Refractive index (20° C.) | 1.4239 | | DIN 51423 |
| Color [mg Pt—Co/l] | 65 | | ISO 6271 |
| Solids [%] | 51.4 | | DIN 38409-1 |
| pH | 8.5 | | 1:1 in water, DIN 38404-C5 |
| $SiO_2$ [%] | 12.5 | 12.2 | see above |
| Ethanol after hydrolysis [%] | 0.2 | | see above |
| Total N [%] | 4.6 | 4.8 | see above |
| Total chloride [%] | 7.6 | 7.3 | see above |
| Hydrol. chloride [%] | 7.1 | 7.3 | see above |

NMR: $^1H$ and $^{13}C$ NMR spectra show the target product (the silane is in a hydrolyzed and oligomerized state) as the main component (about 65% of the silane used):
The formula hereinbelow is an idealized empirical formula of the resulting solid on complete removal of water (cf. corresponding remark in example 2). [$(CH_3)_2N—CH_2—CH_2—N^+(CH_3)_2CH_2—CH_2—CH_2—SiO_{1.5}]_n$ In an aqueous solution, the polymeric product has silanol groups as well as siloxane units.

In addition, unconverted TMEDA and secondary signals are observed. There are no pointers to CPTEO. Presumably, TMEDA which is reacted 2 times is also present.

The $^{29}Si$ NMR spectrum shows: about 2 Si % of silanol (xOH), about 12 Si % of M-structures, about 46 Si % of D-structures, about 40 Si % of T-structures.

Example 4

Waterborne VOC-Free Solution of a Quaternary Silane System Prepared from chloropropyltriethoxysilane and tetramethylethylenediamine. As a Procedural Change, the Total Amount of Water was Added in One Portion Apparatus: Stirred reactor with distilling device, pot thermometer, top thermometer, vacuum pump, manometer and metering device.

Materials Used:

| Inputs | m (input) [g] | n (inputs) [mol] | w (inputs) [%] | Comment |
|---|---|---|---|---|
| Chloropropyltriethoxysilane | 399.8 | 1.66 | 45.77 | M = 240.8 g/mol |
| N,N,N',N'-tetramethylethylenediamine | 193.3 | 1.66 | 22.13 | M = 116.21 g/mol |
| Completely ion-free water | 280.44 | | 32.10 | |
| Σ inputs | 873.54 | | | |

Procedure: A 2 l four-neck flask stirred apparatus is initially charged with CPTEO and TMEDA under agitation. The completely ion-free water is added dropwise at room temperature during 13 min. Severe cloudiness ensues. At a pot temperature of 82-86° C., the contents are heated under reflux for 5.5 h to obtain a liquid containing a white precipitate (insoluble in ethanol or water).

Example 5

Waterborne Solution of a Quaternary Silane System Prepared from 3-chloropropyltriethoxysilane and N,N-dimethylethylenediamine Apparatus:
Stirred reactor with reflux condenser, pot thermometer, top thermometer and metering device.

Materials Used:

| Inputs | m (input) [g] | n (inputs) [mol] | w (inputs) [%] | Comment |
|---|---|---|---|---|
| Chloropropyl-triethoxysilane | 107.79 | 0.448 | 34.1 | M = 240.8 g/mol |
| N,N-Dimethylethylenediamine | 39.44 | 0.447 | 12.5 | M = 88.15 g/mol |
| Completely ion-free water | | | | |
| 1st addition | 41.4 | | 13.1 | |
| 2nd addition | 40.0 | | 12.7 | |
| 3rd addition | 47.1 | | 14.9 | |
| 4th addition | 40.0 | | 12.7 | |
| Σ inputs | 315.7 | | | | m(ethanol after hydrolysis)=61.8 g; final weight of product: 185.4 g, theory: 315.7 g Procedure: A 0.5 l four-neck flask stirred apparatus is initially charged with CPTEO and dimethylethylenediamine under agitation. 41.4 g of completely ion-free water are added dropwise (1st addition) at room temperature within 5 min.

Severe cloudiness ensues and the reaction is slightly exothermic. This is followed by refluxing at a pot temperature of 83 to 85° C. for 4 h and the metered addition of the water during this period in a further three portions to obtain a slightly milky cloudy low-viscosity liquid.

Analyses:

| Determination | Result | Method |
|---|---|---|
| pH | 9.2 | DIN 38404-C5 |
| SiO$_2$ [%] | 6.6 | see above |
| Total N [%] | 3.1 | see above |
| Total chloride [%] | 4.1 | see above |
| Hydrol. chloride [%] | 3.6 | see above |

Example 6

Waterborne VOC-Free Solution of Quaternary Silane System Prepared from 3-chloropropyltrimethoxysilane (CPTMO) and tetramethylethylenediamine Apparatus: Stirred reactor with distilling device, pot thermometer, top thermometer, vacuum pump, manometer and metering device.

Materials Used:

| Inputs | m (input) [g] | n (inputs) [mol] | w (inputs) [%] | Comment |
|---|---|---|---|---|
| Dynasylan ® CPTMO | 330.5 | 1.67 | 35.84 | M = 199.0 g/mol |
| N,N,N',N'-tetramethyl-ethylenediamine | 193.9 | 1.67 | 21.03 | M = 116.21 g/mol |
| Completely ion-free water | | | | |
| 1st addition | 199.8 | | 21.67 | |
| 2nd addition | 79.95 | | 8.67 | |
| 3rd addition | 100.1 | | 10.86 | |
| 4th addition | 17.8 | | 1.93 | |
| Σ inputs | 922.05 | | | | m (ethanol ex hydrolysis) = 160.52 g;
final weight of product after filtration: 648.1 g,
theory: 761.63 g; final weight of distillate: 224.4 g Procedure: A 1 l four-neck flask stirred apparatus is initially charged with CPTMO and TMEDA under agitation. Everything is stirred at 71 to 75° C. for 1.5 h. Thereafter, 199.8 g of completely ion-free water are added dropwise at 71 to 87° C. during 2.4 h to form a slightly cloudy yellowish liquid. During the dropwise addition, the hydrolysis methanol was distilled off under reduced pressure. Then, 79.95 g of completely ion-free water are added dropwise during about 16 min. The next day, 100.1 g of completely ion-free water are added dropwise at a pot temperature of 35° C. to 39° C. during 3 minutes and residual quantities of hydrolysis methanol are then distilled off under reduced pressure. At the end, a further 17.8 g of completely ion-free water are stirred in. Then, the slightly cloudy yellowish product is filtered via pressure filter and Seitz K900 to obtain a clear viscose yellowish liquid.

Analyses:

| Determination | Result | Method |
|---|---|---|
| Viscosity (20° C.) [mPa s] | 450 | DIN 53015 |
| Density (20° C.) [g/ml] | 1.129 | DIN 51757 |

| Determination | Result | Method |
|---|---|---|
| Solids [%] | 56.9 | QM-AA AS-FA-SL 7001 |
| pH | 8.6 | 1:1 in water, DIN 38404-C5 |
| SiO$_2$ [%] | 14.1 | see above |
| Methanol after hydrolysis [%] | 1.5 | see above |
| Free methanol [%] | 1.5 | see above |
| Total chloride [%] | 8.4 | see above |
| Hydrol. chloride [%] | 8.4 | see above |

NMR: Oligomerization is more pronounced (compared with CPTEO-TMEDA reaction). The spectra show the target product (the silane is present in hydrolyzed and oligomerized state) as the main component (about 65% of the silane used).

The formula hereinbelow gives an idealized empirical formula of the resulting solid on complete removal of water (cf. corresponding remark in example 2).

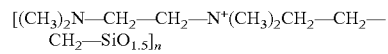

$[(CH_3)_2N-CH_2-CH_2-N^+(CH_3)_2CH_2-CH_2-CH_2-SiO_{1.5}]_n$

In aqueous solution, the polymeric product has silanol groups as well as siloxane units.
TMEDA monoadduct=83.6% TMEDA bisadduct=16.4%

The $^{29}$Si NMR spectrum shows: about 0.7% of silanol (xOH), about 9.0 Si % of M-structures, about 49.6 Si % of D-structures, about 40.7 Si % of T-structures Example 7

Waterborne VOC-Free Solution of a Quaternary Silane System Prepared from 3-chloropropyltrimethoxysilane and tetramethylethylenediamine Using tetramethylethylenediamine in Excess.

Apparatus: stirred reactor with distilling device, pot thermometer, top thermometer, vacuum pump, manometer and metering device.

Materials Used:

| Inputs | m (input) [g] | n (inputs) [mol] | w (inputs) [%] | Comment |
|---|---|---|---|---|
| Dynasylan ® CPTMO | 298.3 | 1.50 | 28.37 | M = 199.0 g/mol |
| N,N,N',N'-tetramethyl-ethylenediamine | 261.8 | 2.25 | 24.93 | M = 116.21 g/mol |
| Completely ion-free water | | | | |
| 1st addition | 49.81 | | 4.74 | |
| 2nd addition | 99.91 | | 9.51 | |
| 3rd addition | 101.08 | | 9.62 | |
| 4th addition | 144.8 | | 13.79 | |
| HCl w = 37% | 94.57 | | 9.00 | |
| Σ inputs | 1050.27 | | | | m (ethanol ex hydrolysis) = 144.18 g;
final weight of product after filtration: 697.9 g
final weight of distillate: 308.9 g Procedure: A 1 l four-neck flask stirred apparatus is initially charged with CPTMO and TMEDA under agitation. Everything is stirred at 60 to 70° C. for 1.5 h. Thereafter, 50 g of completely ion-free water are added dropwise at 80 to 90° C. during 30 min. Thereafter, the system is allowed to react for 30 min and at the same time the resulting methanol is distilled off at normal pressure. Then, 2 further 100 g lots of water are added dropwise during 30 min before the system is allowed to react for a further 30 min to form a clear solution as soon as cloudiness occurs interrupt the addition of water and allow the system to react. After about 145 g of methanol/ water have distilled off, the distillation is discontinued. The CPTMO conversion is determined as difference between w (total chloride) and w (hydr. chloride) CPTMO. After the reaction is ended, the mixture is neutralized with 37% of hydrochloric acid asserting a pH of 7 (exothermic). Then, methanol-water is distilled off at 300 to 100 mbar and a pot temperature of up to about 55° C. When the batch turns viscose, about 100 g of water are added (theoretical amount of hydrolysis methanol for 1.5-molar batch: 144.2 g). About 290 g of methanol-water mixture should be distilled off. At the end, the distillatively removed amount of water is added back. The product is filtered through a SEITZ K900 pressure filter to obtain a clear yellowish slightly viscose liquid.

Analyses:

| Determination | Result | Method |
|---|---|---|
| Viscosity (20° C.) [mPa s] | 286 | DIN 53015 |
| Solids [%] | 68.3 | DIN 38409-1 |
| pH | 7.1 | 1:1 in water, DIN 38404-C5 |
| SiO$_2$ [%] | 12.3 | see above |
| Methanol after hydrolysis [%] | 0.1 | see above |
| Free methanol [%] | 0.1 | see above |

NMR: The spectra show the target product (the silane is in a hydrolyzed and oligomerized state) as the main component (about 85% of the silane used)

The formula hereinbelow gives an idealized empirical formula of the resulting solid on complete removal of water (cf. corresponding remark in example 2).

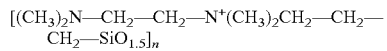

In aqueous solution, the polymeric product has silanol groups as well as siloxane units.

The $^{29}$Si NMR spectrum shows: about 1.5% of silanol (xOH), about 8.4 Si % of M-structures, about 46.7 Si % of D-structures, about 43.4 Si % of T-structures

Example 8

Waterborne VOC-Free Solution of a Quaternary Silane Co-Condensate Prepared from 3-chloropropyltriethoxysilane, 3-aminopropyltriethoxysilane (AMEO) and tetramethylethylenediamine Apparatus: Stirred reactor with distilling device, pot thermometer, top thermometer, vacuum pump, manometer and metering device.

Materials Used:

| Inputs | m (input) [g] | n (inputs) [mol] | w (inputs) [%] | Comment |
|---|---|---|---|---|
| chloropropyl-triethoxysilane | 200.1 | 0.83 | 35.61 | M = 240.8 g/mol |
| N,N,N',N'-tetramethyl-ethylenediamine | 96.7 | 0.83 | 17.21 | M = 116.21 g/mol |
| Completely ion-free water | | | | |
| 1st addition | 100.0 | | 17.80 | |
| 2nd addition | 40.1 | | 7.14 | |
| 3rd addition | 100.1 | | 17.81 | |
| Dynasylan ® AMEO | 24.9 | 0.113 | 4.43 | M = 221.0 g/mol |
| Σ inputs | 561.9 | | | | m (ethanol ex hydrolysis) = 130.20 g,
final weight of product: 413.3 g, theory: 431.7 g;
final weight of distillate: 219.5 g Procedure: A 1 l four-neck flask stirred apparatus is initially charged with CPTEO and TMEDA under agitation. 100.0 g of completely ion-free water are added dropwise (1st addition) at room temperature during 15 min. Severe cloudiness ensues and the reaction is slightly exothermic. This is followed by refluxing at about 90° C. pot temperature for 3 h. Thereafter, Dynasylan® AMEO are added dropwise within about 15 min followed by a further 3 h of heating at about 90° C. pot temperature. Subsequently, 40.0 g of completely ion-free water are added (2nd addition) during 5 min followed by a further 1.5 h of heating at 90° C. Finally, a further 100.0 g of completely ion-free water are added (3rd addition) during 20 min under agitation.

Thereafter, ethanol/water is distilled off (twice the amount of ethanol theoretically formed) at 300-100 mbar and a pot temperature up to about 55° C. When the batch turns viscose, water is quickly added. On completion of the distillation the distillatively removed amount of water is replaced with completely ion-free water and the mixture is cooled down to RT with stirring. The product is filtered through a SEITZ K700 pressure filter to obtain a clear slightly yellow low-viscosity liquid.

Analyses:

| Determination | Result | Method |
|---|---|---|
| Viscosity (20° C.) [mPa s] | 180 | DIN 53015 |
| Density (20° C.) [g/ml] | 1.117 | DIN 51757 |
| Color [mg Pt—Co/l] | 160 | ISO 6271 |
| Solids [%] | 50.1 | DIN 38409-1 |
| pH | 8.5 | 1:1 in water, DIN 38404-C5 |
| SiO$_2$ [%] | 13.5 | see above |
| Ethanol after hydrolysis [%] | 0.1 | see above |
| Total N [%] | 5.0 | see above |
| Total chloride [%] | 7.0 | see above |
| Hydrol. chloride [%] | 7.0 | see above |

Example 9

Preparation of Silanized Silica Dispersions and Production of Papercoating Slips Therefrom: Substances: Polyvinyl Alcohol: Partially Hydrolyzed Polyvinyl Alcohol (from Poval® PVA 235); Boric Acid Solution: 7% by Weight Aqueous Boric Acid Solution A general example of preparation: the silica used is a commercially available pyrogenous silica having a surface area of 200 m$^2$/g, a primary particle size of about 12 nm and an SiO$_2$ content of >99.8% by weight. The pyrogenous silica is incorporated in the aqueous solution by means of a Dispermat dissolver with heavy duty d=60 mm dissolver disk. Post-dispersion is effected using an Ultra Turrax T25 rotor-stator disperser. The coating slip is produced in a glass beaker equipped with a stirring element (magnetic stirrer) from the aqueous silica dispersion by adding a 9.04% by weight aqueous solution of a partially hydrolyzed polyvinyl alcohol from Kuraray, Poval® PVA 235, degree of hydrolysis 87-89%, viscosity 80-110 mPa s, and a 7% by weight aqueous solution of boric acid.

Example 9a

Coating Slip Using butylaminopropyltrimethoxysilane

1. Preparation of silanized silica dispersion: 600.13 g of completely ion-free water and 10.0 g of an aqueous 18% by weight HCl solution are initially charged. A dissolver is used to disperse 248.41 g of pyrogenous silica. This is followed by 10 min postdispersal at 8000-10000 rpm. This is followed by a further homogenization for 10 min using Ultra Turrax at 20500 rpm. Then, 17.14 g of a 20% by weight solution of butylaminopropyltrimethoxysilane in methanol are gradually added together with a further 4.03 g of the 18% by weight hydrochloric acid. In the process, the pH must not exceed a value of about 4, since the dispersion turns very viscous above that value. On completion of the silane addition the mixture is further dispersed for about 60 min using Ultra Turrax at 20500 rpm.

2. Production of a coating slip from 1: 65.15 g of completely ion-free water are initially charged. 74.86 g of the polyvinyl alcohol solution are added with stirring. Then, 124.97 g of the silica dispersion from 1 are stirred in. Thereafter, 12.03 g of the boric acid solution are metered in during 10 min. This is followed by 15 min of stirring. The coating slip has properties reported in the table "Properties of coating slip".

Example 9b

Coating Slip Using an Aqueous Alcohol-Free Hydrolyzate of butylaminopropyl-trimethoxysilane The hydrolyzate is prepared as follows:
Apparatus: 1 l four-neck flask, stirring mechanism equipped with blade stirrer, dropping funnel, thermometer, distillation bridge with vacuum connection, receiver, vacuum pump stand, oil bath with regulator
Materials Used:

| Inputs | m (actual) [g] | Amount of substance [mol] | W/W [%] |
|---|---|---|---|
| Butylaminopropyltrimethoxysilane | 249.53 g | 1.06 mol | 50% |
| Formic acid 85% | 68.10 g | 1.48 mol + 40.6% excess | 13.7% |
| Completely ion-free water | 181.15 g | 10.6 mol | 36.3% |
| Total Σ | 498.8 g | | |

Procedure: completely ion-free water and formic acid are initially charged with stirring and butylaminopropyltrimethoxysilane is added dropwise such that the pot temperature does not exceed 60° C. On completion of the dropwise addition the pH is measured. It should be between pH 4.0-5.0. Add formic acid or butylaminopropyltrimethoxysilane if necessary. This is followed by stirring with the oil bath at a pot temperature of 60° C. for 3 h. Before the methanol is distilled off, 101.9 g of water are added in order that the distillatively removed methanol may be replaced in terms of volume. At a pressure of 130 mbar and a pot temperature of 40-60° C., 203.8 g of methanol/water are distilled off. Then, the final weight of the pot contents are determined and completely ion-free water is added to restore the original mass of 499.0 g.
Analyses (Product):

| Determination | Result | Method |
|---|---|---|
| Total N: | 2.8% (mass) | see above |
| Si content: | 5.9% (mass) | |
| 1H NMR: | per n-butylaminosilyl radical: 1.2 mol of formate, 0.05 mol of methanol | |

| Determination | Result | Method |
|---|---|---|
| 29Si NMR: | 1% of monomers 5% of Si-M- 37% of Si-D- 57% of Si-T-structures | |
| pH: | 4.6 | DIN 38404 |
| Solids content: | 44.0% (mass) | Cf. QM-AA |
| Viscosity (20° C.) | 27.9 mPa s | DIN 53015 |
| Methanol after hydrolysis | 0.6% (mass) | see above |
| Free methanol | 0.6% (mass) | |
| SiO₂ content | 12.7% (mass) | see above |
| Density (20° C.) | 1.012 g/cm3 | DIN 51757 |

1. Preparation of silanized silica dispersion: 600.02 g of completely ion-free water and 5.95 g of an aqueous 18% by weight HCl solution are initially charged. A dissolver is used to disperse 260.84 g of pyrogenous silica. This is followed by 15 min postdispersal at 5000-7000 rpm. This is followed by a further homogenization for 10 min using Ultra Turrax at 20500 rpm. Then, 34.16 g of the silane hydrolyzate are gradually added with a further 1.37 g of the 18% by weight hydrochloric acid. In the process, the pH must not exceed a value of about 3, since the dispersion turns very viscous above that value. On completion of the silane addition the mixture is further dispersed for about 60 min using Ultra Turrax at 20500 rpm.

2. Production of a coating slip from 1: 65.52 g of completely ion-free water are initially charged. 75.30 g of the polyvinyl alcohol solution are added with stirring. Then, 125.42 g of the silica dispersion from 1 are stirred in. Thereafter, 12.00 g of the boric acid solution are metered in during 10 min. This is followed by 15 min of stirring. The coating slip has properties reported in the table "Properties of coating slip".

Example 9c

Coating Slip Using an Aqueous Alcohol-Free Hydrolyzate of butylaminopropyltrimethoxysilane The hydrolyzate is prepared as described under example 9b.

1. Preparation of silanized silica dispersion: 600.62 g of completely ion-free water are initially charged. A dissolver is used to disperse 259.45 g of pyrogenous silica. This is followed by 15 min postdispersal at 5000-7000 rpm. This is followed by a further homogenization for 10 min using Ultra Turrax at 20500 rpm. Thereafter, 4.82 g of an 85% by weight formic acid solution in water are added. Then, 68.59 g of the silane hydrolyzate are gradually added. In the process, the pH must not exceed a value of about 4, since the dispersion turns very viscous above that value. On completion of the silane addition the mixture is further dispersed for about 60 min using Ultra Turrax at 20500 rpm.

2. Production of a coating slip from 1: 65.11 g of completely ion-free water are initially charged. 75.35 g of the polyvinyl alcohol solution are added with stirring. Then, 125.34 g of the silica dispersion from 1 are stirred in. Thereafter, 12.08 g of the boric acid solution are metered in during 10 min. This is followed by 15 min of stirring. The coating slip has properties reported in the table "Properties of coating slip".

Example 9d

Coating Slip Using the Aqueous Alcohol-Free Quaternary Aminosilane System from Example 1

1. Preparation of silanized silica dispersion: 300.04 g of completely ion-free water and 7.07 g of an aqueous 18% by weight HCl solution are initially charged. A dissolver is used to disperse 129.34 g of pyrogenous silica. This is followed by 15 min postdispersal at 4000 rpm. This is followed by a further homogenization for 10 min using Ultra Turrax at 20500 rpm. Then, 31.20 g of the silane hydrolyzate are gradually added with a further 1.65 g of the 18% by weight hydrochloric acid. In the process, the pH must not exceed a value of about 3, since the dispersion turns very viscose above that value. On completion of the silane addition the mixture is further dispersed for about 60 min using Ultra Turrax at 20500 rpm.
2. Production of a coating slip from 1: 65.00 g of completely ion-free water are initially charged. 76.08 g of the polyvinyl alcohol solution are added with stirring. Then, 127.25 g of the silica dispersion from 1 are stirred in. Thereafter, 12.05 g of the boric acid solution are metered in during 10 min. This is followed by 15 min of stirring. The coating slip has properties reported in the table "Properties of coating slip".

Example 9e

Coating Slip Using an Alcohol-Containing Quaternary Aminosilane

The quaternary aminosilane is prepared as follows:
Water-free ethanolic quaternary silane system prepared from chloropropyltriethoxysilane and tetramethylethylenediamine.

Apparatus: Büchi autoclave with pot thermometer, manometer and N2 blanket

Materials Used:

| Inputs | m (input) [g] | n (inputs) [mol] | w (inputs) [%] | Comment |
|---|---|---|---|---|
| Chloropropyl-triethoxysilane | 216.7 | 0.9 | 25.7 | M = 240.8 g/mol |
| N,N,N',N'-tetramethyl-ethylenediamine | 104.6 | 0.9 | 12.4 | M = 116.21 g/mol |
| Ethanol | 520.7 | | 61.8 | |

Final weight of product: 718.0 g, theory: 751.3 g; total amount of samples: 90.7 g Procedure:
Chloropropyltriethoxysilane is initially charged, and tetramethylethylenediamine and ethanol are rapidly added with stirring. The reaction is then carried out in the autoclave at a pot temperature of 140° C. The overpressure rises to about 4.3 bar in the process. The reaction is policed time-dependently using GC. Extending the reaction time from 5 h to 10 h leads to a distinct reduction in chloropropyltriethoxysilane at almost constant TMEDA content: reaction as far as the bisadduct. A conversion of >90% was reached after a reaction time of 10 h. White precipitations formed to a minimal extent in the pot. They were filtered off, washed with n-heptane and dried in a rotary evaporator: m=5.0 g.

Analyses (Product):

| Determination | Result | Method |
|---|---|---|
| Density (20° C.) [g/ml] | 0.856 | DIN 51757 |
| $SiO_2$ [%] | 6.6 | see above |
| Total N [%] | 2.8 | see above |
| Total chloride [%] | 3.5 | see above |
| Hydrol. chloride [%] | 3.5 | see above |

1. Preparation of silanized silica dispersion: 600.33 g of completely ion-free water and 9.65 g of an aqueous 18% by weight HCl solution are initially charged. A dissolver is used to disperse 248.79 g of pyrogenous silica. This is followed by 15 min postdispersal at 6000 rpm. This is followed by a further homogenization for 10 min using Ultra Turrax at 20500 rpm. Then, 66.81 g of the ethanolic silane solution are gradually added together with a further 4.57 g of 18% by weight hydrochloric acid. In the process, the pH must not exceed a value of about 3.5, since the dispersion turns very viscose above that value. On completion of the silane addition the mixture is further dispersed for about 60 min using Ultra Turrax at 20500 rpm.
2. Production of a coating slip from 1: 64.94 g of completely ion-free water are initially charged. 75.81 g of the polyvinyl alcohol solution are added with stirring. Then, 126.95 g of the silica dispersion from 1 are stirred in. Thereafter, 12.04 g of the boric acid solution are metered in during 10 min. This is followed by 15 min of stirring. The coating slip has properties reported in the table which follows.

Table of "Properties of coating slips":

| | Example | | | | |
|---|---|---|---|---|---|
| | 9a | 9b | 9c | 9d | 9e |
| Silane content of silica dispersion/wt % | 1.8 | 1.9 | 3.7 | 3.7 | 1.9 |
| Alcohol content of silica dispersion/wt % | 7.9 | 0.0 | 0.0 | 0.0 | 6.4 |
| Viscosity of coating slip/mPa s | 129 | 589 | 174 | 83 | 423 |

It is evident from the table that alcoholic aminosilane solutions (example 9a) can be used to obtain low-viscosity coating slips having a viscosity <150 mPa s. Using the same silane in the form of the waterborne alcohol-free hydrolyzate provides acceptable viscosities below 300 mPa s only at nearly double the dose (example 9c). When waterborne quaternary aminosilane solutions are used (example 9d), the same dose (comparison with waterborne aminosilane) provides excellent viscosities below 100 mPa s. The same active silane substance, by contrast, when used as nonhydrolyzed alcoholic solution, provides a nonacceptable viscosity to the coating slip and also a high, problematic alcohol content.

The invention claimed is:
1. A process for preparing a composition containing quaternary amino-functional organosilicon compounds, comprising reacting
    as component A
    (i) at least one haloalkyl-functional alkoxysilane of the general formula I

$(R^1O)_{3-x-y}(R^2)_x Si[(R^3)_n CH_2 Hal]_{1+y}$  (I), where the $R^1$ groups are the same or different and $R^1$ represents a hydrogen, a linear, branched, or cyclic alkyl group having 1 to 8 carbon atoms, an aryl, arylalkyl or acyl group, the $R^2$ groups are the same or different and $R^2$ represents a linear, branched or cyclic alkyl group having 1 to 8 carbon atoms, or an aryl, arylalkyl or acyl group, the $R^3$ groups are the same or different and $R^2$ signifies a linear, branched or cyclic alkylene group having 1 to 18 carbon atoms, n is equal to 0 or 1 and Hal represents chlorine or bromine, and x is equal to 0, 1 or 2, y is equal to 0, 1 or 2 and (x+y) is equal to 0, 1 or 2, or (ii) a hydrolysis or condensation product of at least one alkoxysilane of the aforementioned general formula I or (iii) a mixture of at least one alkoxysilane of the aforementioned general formula I and a hydrolysis and/or condensation product of at least one alkoxysilane of the aforementioned general formula I, with a tertiary amine of the general formula II as component B, $$N(R^4)_3 \qquad (II),$$

wherein the $R^4$ groups are the same or different and represent a linear, branched or cyclic alkyl group having 1 to 30 carbon atoms which may additionally be substituted, where optionally two $R^4$ groups are in turn linked together and combine with the nitrogen of the tertiary amine to form a cycle, and, with at least one further hydrolyzable/condensable silicon compound as component C, wherein component C comprises at least one organofunctionalized silicon compound of formula III, its hydrolysis products, condensation products, co- or block condensation products or mixtures thereof, $$(R^7O)_{3-a-b}(R^8)_a Si(B)_{1+b} \qquad (III)$$

where $R^7$ in each occurrence independently represents a hydrogen, a linear, branched or cyclic alkyl group having 1 to 8 carbon atoms, an aryl, arylalkyl or acyl group, $R^8$ in each occurrence independently signifies a linear, branched or cyclic alkyl group having 1 to 24 carbon atoms, an aryl or arylalkyl group, the B groups are the same or different and B represents an organofunctional group, a is equal to 0, 1 or 2, b is equal to 0, 1 or 2 and (a+b) is equal to 0, 1 or 2, wherein the compound of the general formula III is selected from compounds with B being equal to —$[(R^{10})_n R^9]$, where $R^{10}$ represents a linear, branched or cyclic alkylene or alkenylene group having 1 to 18 carbon atoms, n is equal to 0 or 1 and $R^9$ is a substituted or unsubstituted linear, branched or cyclic alkyl group having 1 to 30 carbon atoms which may optionally include one or more —$N(R^{3*})_2$, —$OR^{3*}$ and/or $SR^{3*}$ groups, with $R^{3*}$ in each occurrence independently representing hydrogen or with $R^{3*}$ equal to $R^9$ and also $R^9$ together with a heteroatom N, S or O being a cyclic or heteroaromatic group having 1 to 7 carbon atoms, B being equal to $(R^{5*}O)_{3-x*}(R^{6*})_{x*}Si[(R^{2*})CH_2]$—, where $R^{5*}$ in each occurrence independently represents hydrogen, a linear, branched or cyclic alkyl group having 1 to 8 carbon atoms or represents an aryl, arylalkyl or acyl group, $R^{6*}$ in each occurrence independently signifies a linear, branched or cyclic alkyl group having 1 to 24 carbon atoms or an aryl, arylalkyl or acyl group, $R^{2*}$ is a linear, branched or cyclic alkylene or alkenylene group having 1 to 18 carbon atoms, and $x^*$ is equal to 0, 1 or 2, B is a primary, secondary or tertiary amino-functional radical of the general formulae IIIa, IIIb or IIIc $$R^{11}_{h^*}NH_{(2-h^*)}[(CH_2)_h(NH)]_j[(CH_2)_l(NH)]_c(CH_2)_k— \qquad (IIIa)$$

where $0 \le h \le 6$; $h^*=0$, 1 or 2, $j=0$, 1 or 2; $0 \le l \le 6$; $c=0$, 1 or 2; $0 \le k \le 6$ and $R^{11}$ corresponds to a benzyl, aryl, vinyl or formyl radical or a linear, branched or cyclic alkyl radical having 1 to 8 carbon atoms;

$$[NH_2(CH_2)_d]_2N(CH_2)_p— \qquad (IIIb)$$

where $0 \le d \le 6$ and $0 \le p \le 6$, $$—(CH_2)_{i^*}[NH(CH_2)_{j^*}]_{g^*}NH[(CH_2)_{p^*}NH]_{g^*}(CH_2)_{i^*}SiR^{2*}_{a^*}(OR^{1**})_{b^*} \qquad (IIIc)$$

where i*, f* or g* are each independently identical or different, with i*=0 to 8, f*=1, 2 or 3, g*=0, 1 or 2 and $R^{1**}$ corresponding to a linear, cyclic or branched alkyl radical having 1 to 4 carbon atoms, where i* is more particularly one of the numbers 1, 2, 3 or 4, with a* and b*=0, 1, 2 or 3 and (a*+b*) equal to 3 and $R^{2*}$ is an alkyl radical having 1 to 24 carbon atoms, B is a radical $R^{12}$—$Y_q$—$(CH_2)_s$—, where $R^{12}$ corresponds to a mono-, oligo- or perfluorinated alkyl radical having 1 to 20 carbon atoms or to a mono-, oligo- or perfluorinated aryl radical, where Y corresponds to a —$CH_2$—, —O—, -aryl-, or —S— radical, q is equal to 0 or 1 and s is equal to 0 or 2, more particularly B corresponds to a perfluorinated alkyl radical having from 1 to 20 carbon atoms, B is a vinyl, allyl, isopropenyl, mercaptoalkyl, sulfanealkyl, ureidoalkyl, acryloyloxyalkyl, or methacryloyloxyalkyl radical, more particularly a methacryloyloxypropyl radical, or a linear, branched or cyclic alkoxy radical having 1 to 24 carbon atoms, B is a hydroxyalkyl, epoxy and/or ether radical, more particularly a 3-glycidyloxyalkyl, 3-glycidyloxypropyl, dihydroxyalkyl, epoxyalkyl, epoxycycloalkyl, polyalkylglycolalkyl or a polyalkylglycol-3-propyl radical, or a partial hydrolysis and condensation product of one or at least two compounds of formula III, in the presence of a defined amount of water, and removing the resulting hydrolysis alcohol at least partially from the system.

2. The process according to claim 1, wherein the reaction is carried out in the presence of a catalyst and/or under addition of a separate catalyst.

3. The process according to claim 1, wherein water is used in an amount of 0.5 to 500 mol of water per mole of silicon atoms present in the reaction mixture, concerning the used components A and also optionally B and/or C.

4. The process according to claim 1, wherein the water is metered continuously or discontinuously into the reaction mixture of the input components A, B and optionally C.

5. The process according to claim 1, wherein the reaction is carried out at a pressure in the range from 1 mbar to 1.1 bar.

6. The process according to claim 1, wherein volatile solvent/diluent medium and any groups hydrolyzable to volatile solvent, more particularly hydrolysis alcohol, are removed down to a level in the overall composition of below 12% by weight to 0% by weight, wherein the removing of volatile solvent/diluent medium can be effected during the reaction and/or thereafter by distillation.

7. The process according to claim 1, wherein component A comprises at least one silicon compound from the series 3-chloropropyltrimethoxysilane, 3-chloropropyltriethoxysilane, 3-chloropropylmethyldimethoxysilane, 3-chloropropylmethyldiethoxysilane, 3-chloropropyldimethylethoxysilane or 3-chloropropyldimethylmethoxysilane or a hydrolysis or condensation product of the aforementioned alkoxysilanes.

8. The process according to claim 1, wherein component B comprises at least one tertiary amine represented by of formulae IIa and/or IIb,

where $R^{14}$ in each occurrence independently represents a branched, unbranched or cyclic alkyl, aryl or alkylaryl group having 1 to 20 carbon atoms and h is equal to 0, 1, 2, 3, 4, 5, 6 or 7,

where w is equal to 2 to 20, more particularly where w is equal to 7 to 17, and $R^{14}$ in each occurrence independently represents a branched, unbranched or cyclic alkyl, aryl or alkylaryl group having 1 to 20 carbon atoms and p* is equal to 1 or 2.

9. The process according to claim 1, wherein component B comprises at least one tertiary amine selected from the series tetramethylethylenediamine, pentamethyldiethylenetriamine, hexadecyldimethylamine, octadecyldimethylamine, tetradecyldimethylamine, dodecyldimethylamine, decyldimethylamine, octyldimethylamine, tetraethylethylenediamine, pentaethyldiethylenetriamine, hexadecyldiethylamine, octadecyldiethylamine, tetradecyldiethylamine, dodecyldiethylamine, decyldiethylamine, octyldiethylamine, isohexadecyldimethylamine, isooctadecyldimethylamine, isotetradecyldimethylamine, isododecyldimethylamine, isodecyldimethylamine, isooctyldimethylamine, isotetraethylethylenediamine, isopentaethyldiethylenetriamine, isohexadecyldiethylamine, isooctadecyldiethylamine, isotetradecyldiethylamine, isododecyldiethylamine, isodecyldiethylamine, or isooctyldiethylamine.

10. The process according to claim 1, wherein components A and B are used in a ratio, wherein the molar ratio of the silicon compound within the meaning of formula I to the tertiary amine compound within the meaning of formula II is in the range from 2:1 to 1:m, wherein m is the number of tertiary amine groups of formula II and m is an integer between 1 to 100.

11. The process according to claim 1, wherein components A and C are used in a molar ratio of 1:<4.

12. The process according to claim 1, wherein component C comprises at least one silicon compound from the series silicon tetrachloride, tetramethoxysilane, tetraethoxysilane, tetrapropoxysilane, methyltrimethoxysilane, methyltriethoxysilane, ethyltrimethoxysilane, ethyltriethoxysilane, n-propyltrimethoxysilane, n-propyltriethoxysilane, n-butyltrimethoxysilane, i-butyltrimethoxysilane, n-butyltriethoxysilane, i-butyltriethoxysilane, n-octyltrimethoxysilane i-octyltrimethoxysilane, n-octyltriethoxysilane, i-octyltriethoxysilane, hexadecyltrimethoxysilane, hexadecyltriethoxysilane, vinyltriethoxysilane, vinyltrimethoxysilane, vinyltris(2-methoxyethoxy)silane, phenyltrimethoxysilane, phenyltriethoxysilane, tridecafluoro-1,1,2,2-tetrahydrooctyltrimethoxysilane, tridecafluoro-1,1,2,2-tetrahydrooctyltriethoxysilane, 3-mercaptopropyltrimethoxysilane, 3-mercaptopropyltriethoxysilane, 1-mercaptomethyltrimethoxysilane, 1-mercaptomethyltriethoxysilane, 3-glycidyloxypropyltriethoxysilane, 3-glycidyloxypropyltrimethoxysilane, 3-methacryloxyisobutyltrimethoxysilane, 3-methacryloxyisobutyltriethoxysilane, 3-methacryloxypropyltrimethoxysilane, 3-methacryloxypropyltriethoxysilane, 3-methacryloxypropylmethyldimethoxysilane, 3-methacryloxypropylmethyldiethoxysilane, 3-ureidopropyltriethoxysilane, 3-ureidopropyltrimethoxysilane, 3-aminopropyltrimethoxysilane, 3-aminopropyltriethoxysilane, 3-aminopropylmethyldimethoxysilane, 3-aminopropylmethyldiethoxysilane, 1-aminomethyltrimethoxysilane, 1-aminomethyltriethoxysilane, 2-aminoethyltrimethoxysilane, 2-aminoethyltriethoxysilane, 3-aminoisobutyltrimethoxysilane, 3-aminoisobutyltriethoxysilane, N-n-butyl-3-aminopropyltriethoxysilane, N-n-butyl-3-aminopropylmethyldiethoxysilane, N-n-butyl-3-aminopropyltrimethoxysilane, N-n-butyl-3-aminopropylmethyldimethoxysilane, N-n-butyl-1-aminomethyltriethoxysilane, N-n-butyl-1-aminomethyldimethoxysilane, N-n-butyl-1-aminomethyltrimethoxysilane, N-n-butyl-1-aminomethylmethyltriethoxysilane, benzyl-3-aminopropyltrimethoxysilane, benzyl-3-aminopropyltriethoxysilane, benzyl-2-aminoethyl-3-aminopropyltrimethoxysilane, benzyl-2-aminoethyl-3-aminopropyltriethoxysilane, N-formyl-3-aminopropyltriethoxysilane, N-formyl-3-aminopropyltrimethoxysilane, N-formyl-1-aminomethylmethyldimethoxysilane, N-formyl-1-aminomethylmethyldiethoxysilane, diaminoethylene-3-propyltrimethoxysilane, diaminoethylene-3-propyltriethoxysilane, triaminodiethylene-3-propyltrimethoxysilane, triaminodiethylene-3-propyltriethoxysilane, (2-aminoethylamino)ethyltrimethoxysilane, (2-aminoethylamino)ethyltriethoxysilane, (1-aminoethylamino)methyltrimethoxysilane, (1-aminoethylamino)methyltriethoxysilane, tris(trimethoxysilylpropyl)amine, tris(triethoxysilylpropyl)amine, tris(trimethoxysilylmethyl)amine, tris(triethoxysilylmethyl)amine, bis(trimethoxysilylpropyl)amine, bis(triethoxysilylpropyl)amine, bis(diethoxymethylsilylpropyl)amine, bis(dimethoxymethylsilylpropyl)amine, bis(triethoxysilylmethyl)amine, bis(trimethoxysilylmethyl)amine, bis(diethoxymethylsilylmethyl)amine, bis(dimethoxymethylsilylmethyl)amine,

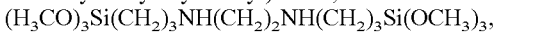
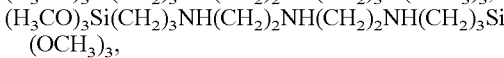

or a mixture of at least two of the aforementioned compounds or a hydrolysis/condensation product of one of the aforementioned compounds or a hydrolysis, condensation, co-, block or block co-condensation product of at least two of the aforementioned compounds.

13. The process according to claim 1, wherein the components A and B and optionally C are mixed, wherein the mixture may optionally have added to it a solvent/diluent medium, water is continuously or discontinuously metered into the mixture in an amount of 0.5 to 500 mol of water per mole of silicon atoms present, and optionally a catalyst is added to the reaction mixture, the reaction mixture present is set to a temperature between 20 and 150° C. at ambient pressure or reduced pressure, and the resultant hydrolysis alcohol is at least partially removed from the reaction mixture as is any solvent/diluent medium used, and the composition thus obtained is optionally diluted with water and thereafter optionally admixed or contacted with at least one further component from the series of pigments, fillers, binders, crosslinkers, optical brighteners, thickeners, rheological auxiliaries, coating auxiliaries or some other auxiliary.

14. A composition containing quaternary aminoalkyl-functional organosilicon compounds and water, obtainable by a process according to claim 1.

15. The composition according to claim 14, wherein a level of active ingredient in the composition ranging from 0.1% to 99.9% by weight, wherein all the constituents in the composition sum to 100% by weight.

16. The composition according to claim 14, wherein a level of water ranging from 0.0999% to 99.9% by weight and a level of volatile solvent/hydrolysis alcohol in the overall composition of below 12% by weight to 0% by weight, wherein all the constituents in the composition sum to 100% by weight.

17. The composition according to claim 14, wherein the composition contains at least one further of the following components from the series pigments, fillers, binders, crosslinkers, optical brighteners, coating auxiliaries or other auxiliaries.

18. The composition according to claim 14, wherein the composition has a viscosity of <1500 mPa s.

19. A method of modifying, treating or producing at least one composition of matter selected from the group consisting of formulations, substrates, articles, organic or inorganic materials, composite materials, papercoating slips, inkjet applications, papercoating materials, paper, textiles, fillers, biocidally, fungicidally and/or virucidally acting formulations, biocidally, fungicidally and/or virucidally acting coatings, fiber materials, yarns, or surfaces, comprising modifying, treating or producing the composition of matter with a composition according to claim 14.

20. The method of claim 19, wherein the composition of matter is selected from the group consisting of sheetlike, fibrous, woven, granular and/or pulverulent materials.

* * * * *

UNITED STATES PATENT AND TRADEMARK OFFICE
CERTIFICATE OF CORRECTION

PATENT NO. : 8,979,996 B2  
APPLICATION NO. : 14/242433  
DATED : *March 17, 2015  
INVENTOR(S) : Burkhard Standke et al.

It is certified that error appears in the above-identified patent and that said Letters Patent is hereby corrected as shown below:

On the title page, Item (54) and in the Specification, Column 1, the Title is incorrect. Item (54) and Column 1 should read:

--COMPOSITION CONTAINING QUATERNARY AMINO-FUNCTIONAL ORGANOSILICON COMPOUNDS AND PRODUCTION AND USE THEREOF--

Signed and Sealed this  
Thirtieth Day of June, 2015

Michelle K. Lee  
*Director of the United States Patent and Trademark Office*